(12) United States Patent
Tang et al.

(10) Patent No.: US 7,070,964 B2
(45) Date of Patent: Jul. 4, 2006

(54) EPOTHILONE COMPOUNDS AND METHODS FOR MAKING THE SAME

(75) Inventors: Li Tang, Foster City, CA (US); Brian Metcalf, Moraga, CA (US); Leonard Katz, Oakland, CA (US); Gary Ashley, Alameda, CA (US)

(73) Assignee: Kosan Biosciences Incorporated, Hayward, CA (US)

( * ) Notice: Subject to any disclaimer, the term of this patent is extended or adjusted under 35 U.S.C. 154(b) by 482 days.

(21) Appl. No.: 10/295,342

(22) Filed: Nov. 14, 2002

(65) Prior Publication Data
US 2003/0219877 A1    Nov. 27, 2003

Related U.S. Application Data

(60) Provisional application No. 60/334,734, filed on Nov. 15, 2001.

(51) Int. Cl.
*C12P 17/00*    (2006.01)
(52) U.S. Cl. ........................ 435/118; 435/120
(58) Field of Classification Search ................ 435/118, 435/120
See application file for complete search history.

(56) References Cited

U.S. PATENT DOCUMENTS 6,583,290 B1 *  6/2003  Julien et al. ................. 548/203
6,921,650 B1 *  7/2005  Julien et al. ................... 435/76

FOREIGN PATENT DOCUMENTS

WO    WO 00/39276    7/2000
WO    WO 01/83800    11/2001

OTHER PUBLICATIONS

PCT International Preliminary Examination Report for PCT/US02/36814.

* cited by examiner

*Primary Examiner*—Francisco C. Prats
(74) *Attorney, Agent, or Firm*—Gary W. Ashley

(57) ABSTRACT

The present invention provides bioconversion methods for making epothilone analogs. These analogs differ from the starting material by the addition of one or more hydroxyl groups or by the addition of an epoxide. These compounds, in turn, can be further modified by chemical synthesis.

1 Claim, 18 Drawing Sheets

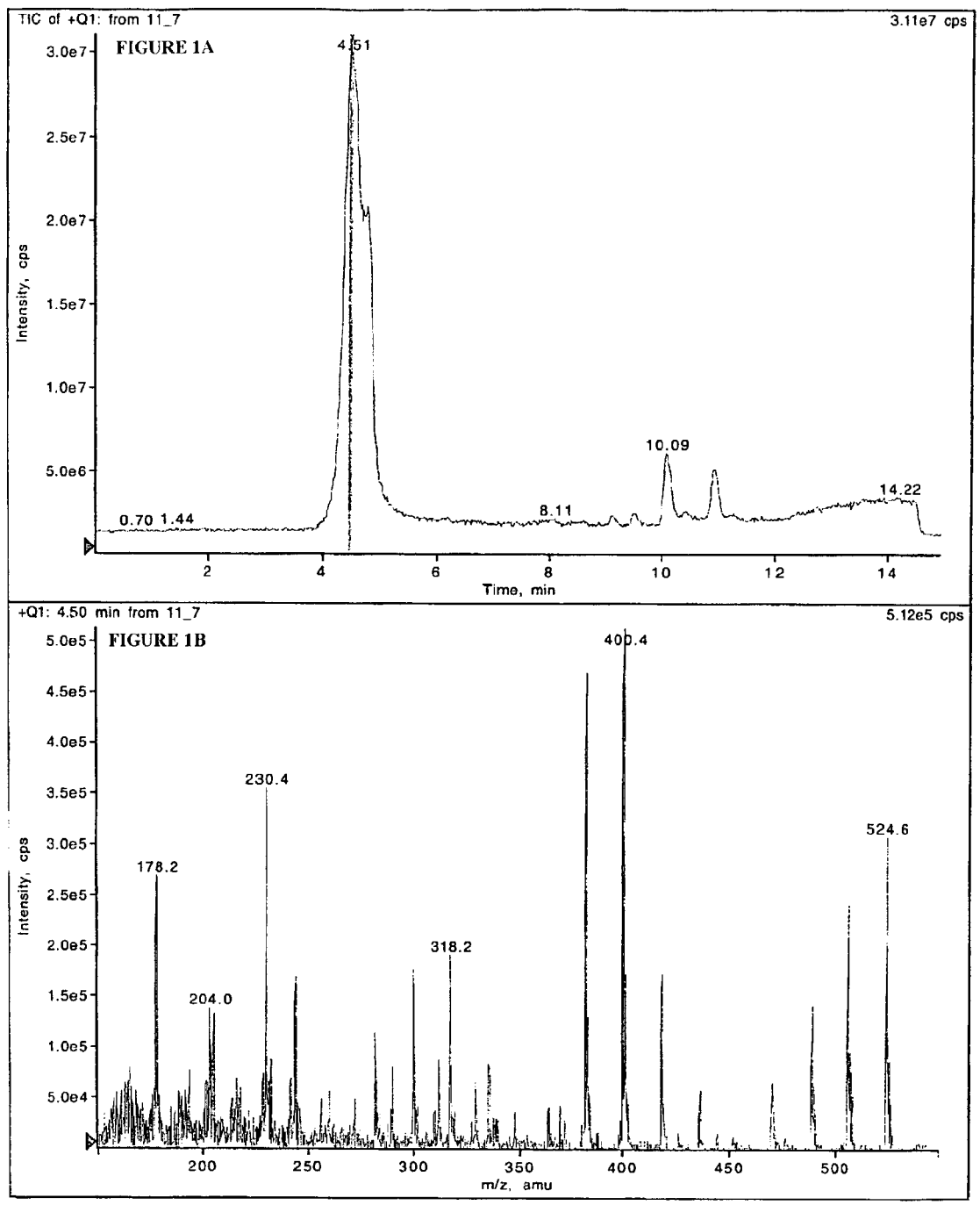

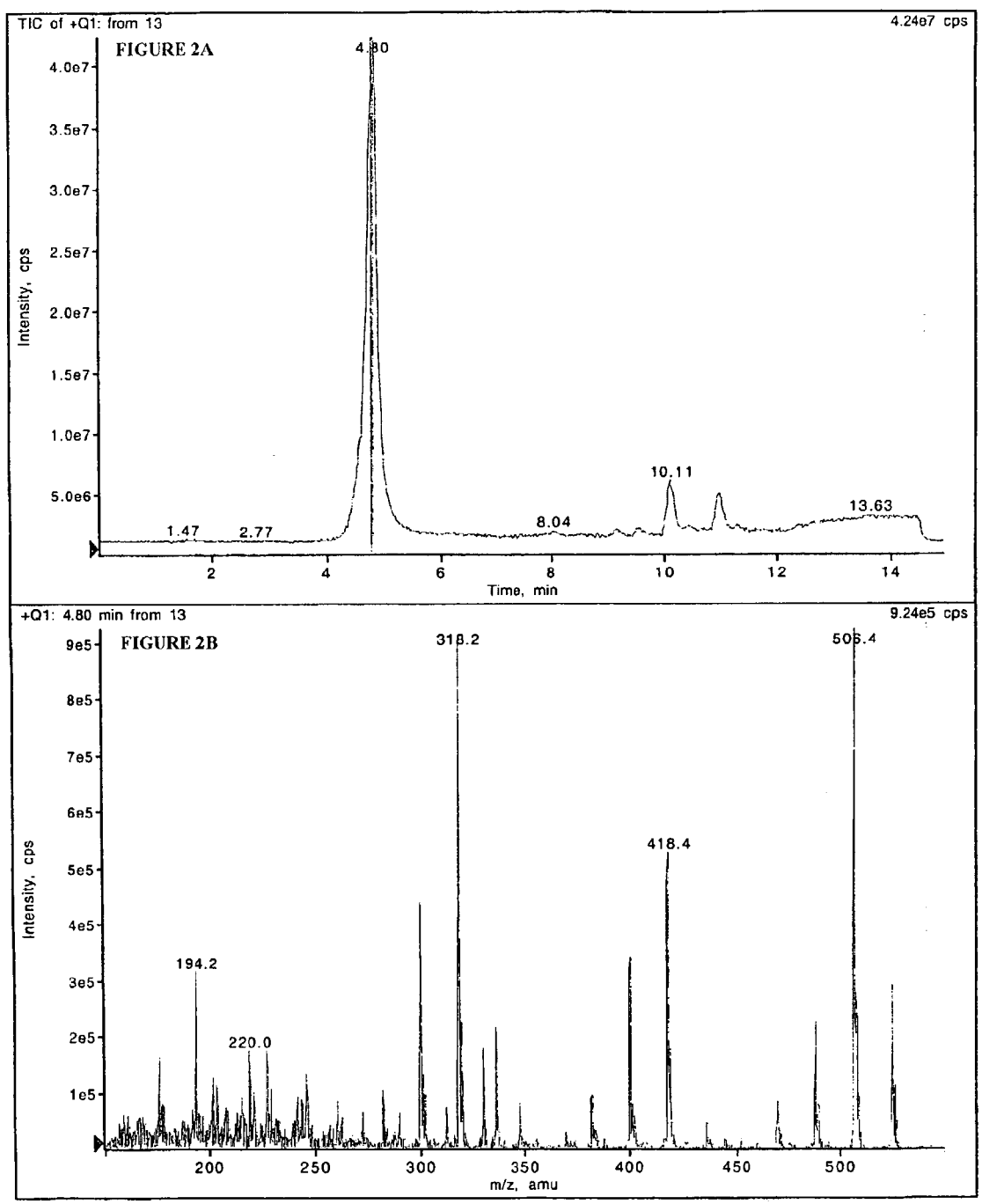

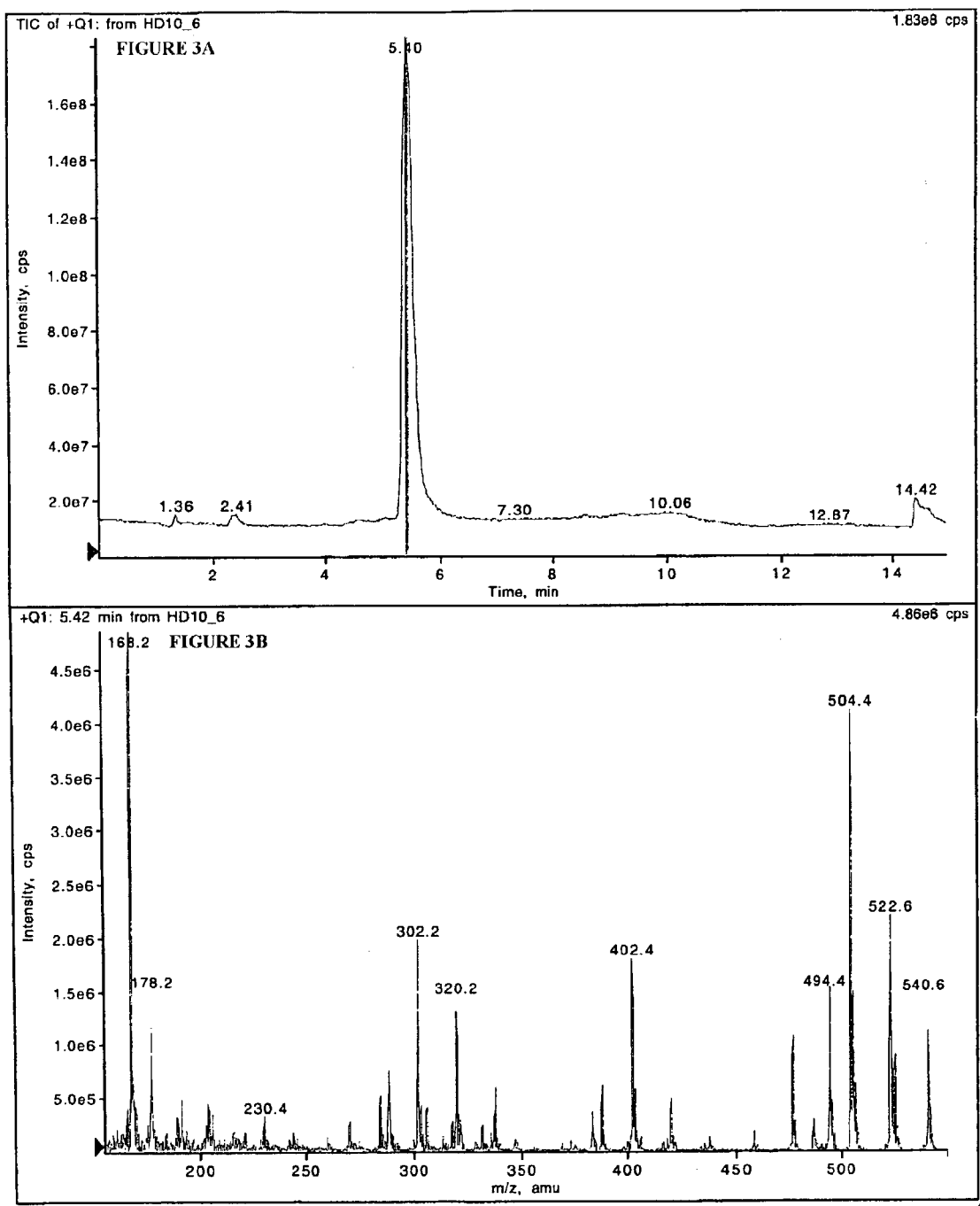

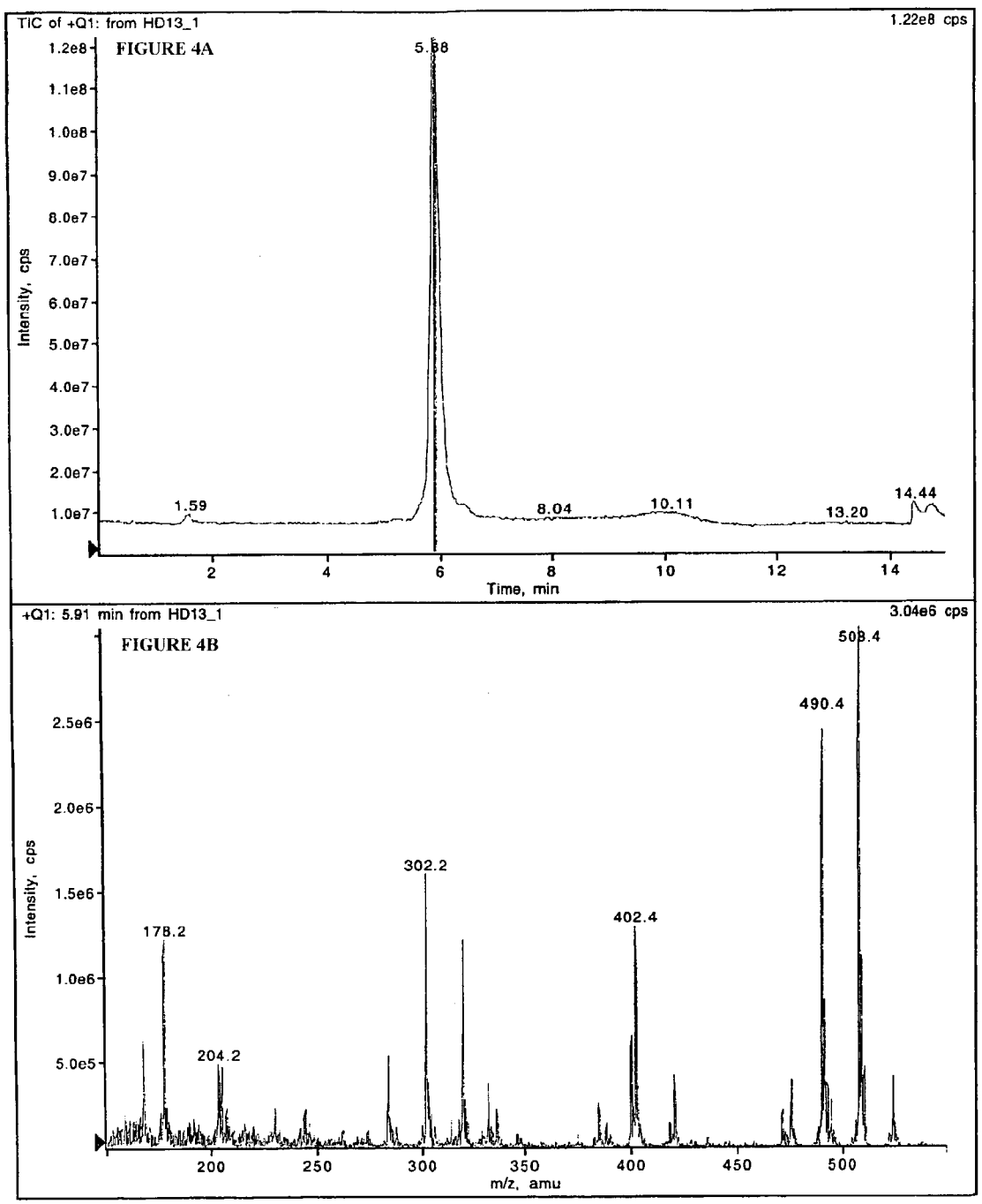

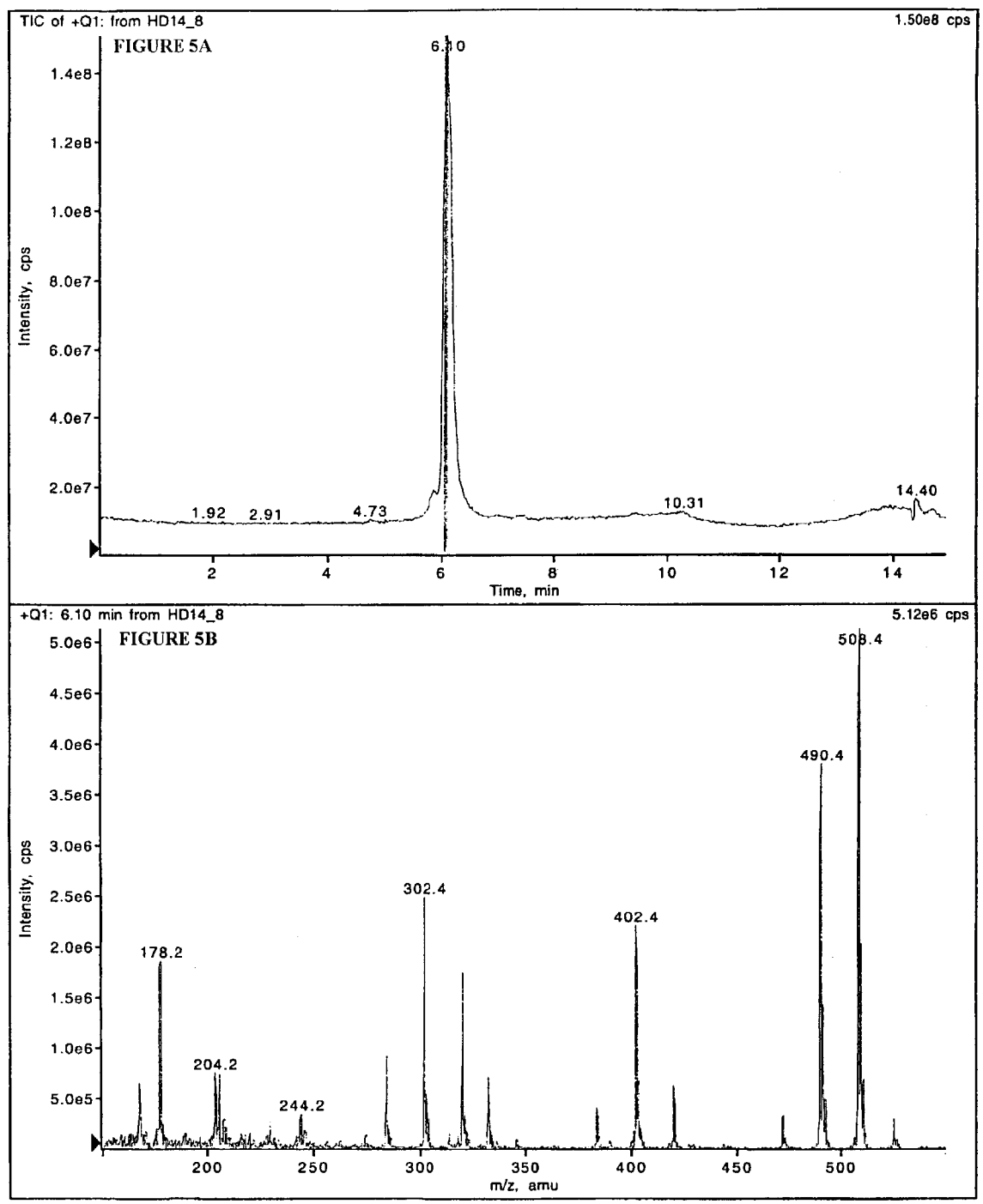

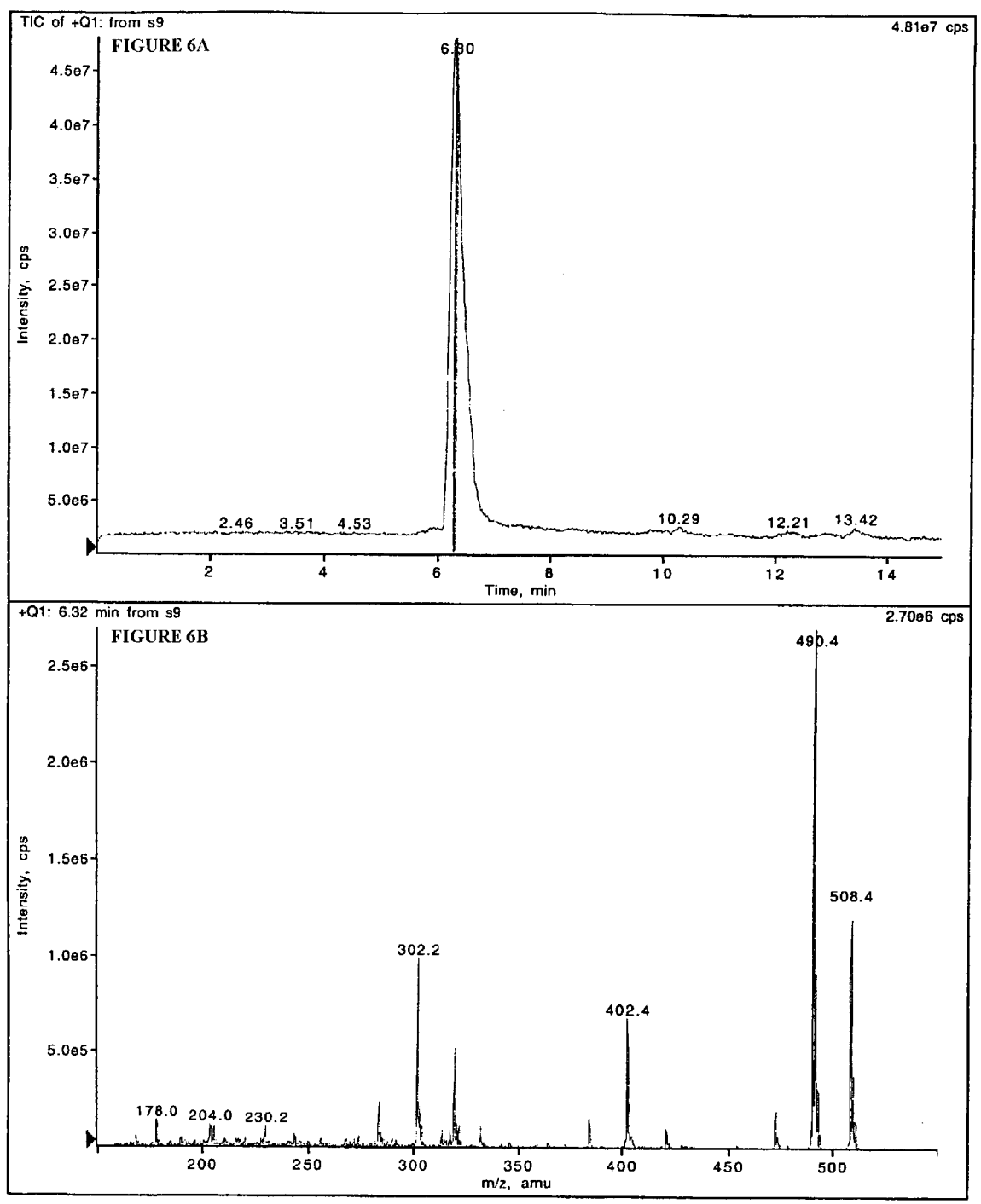

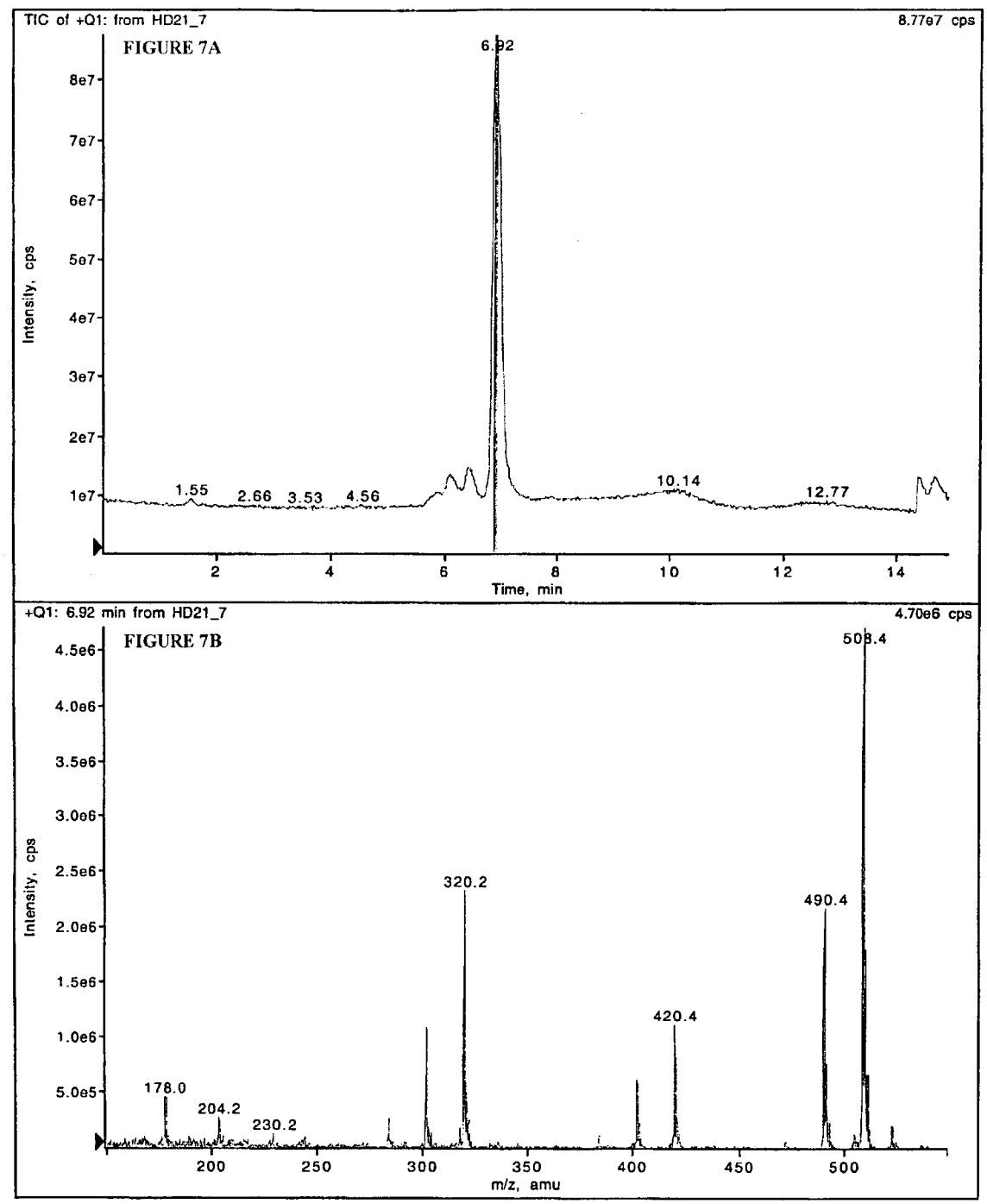

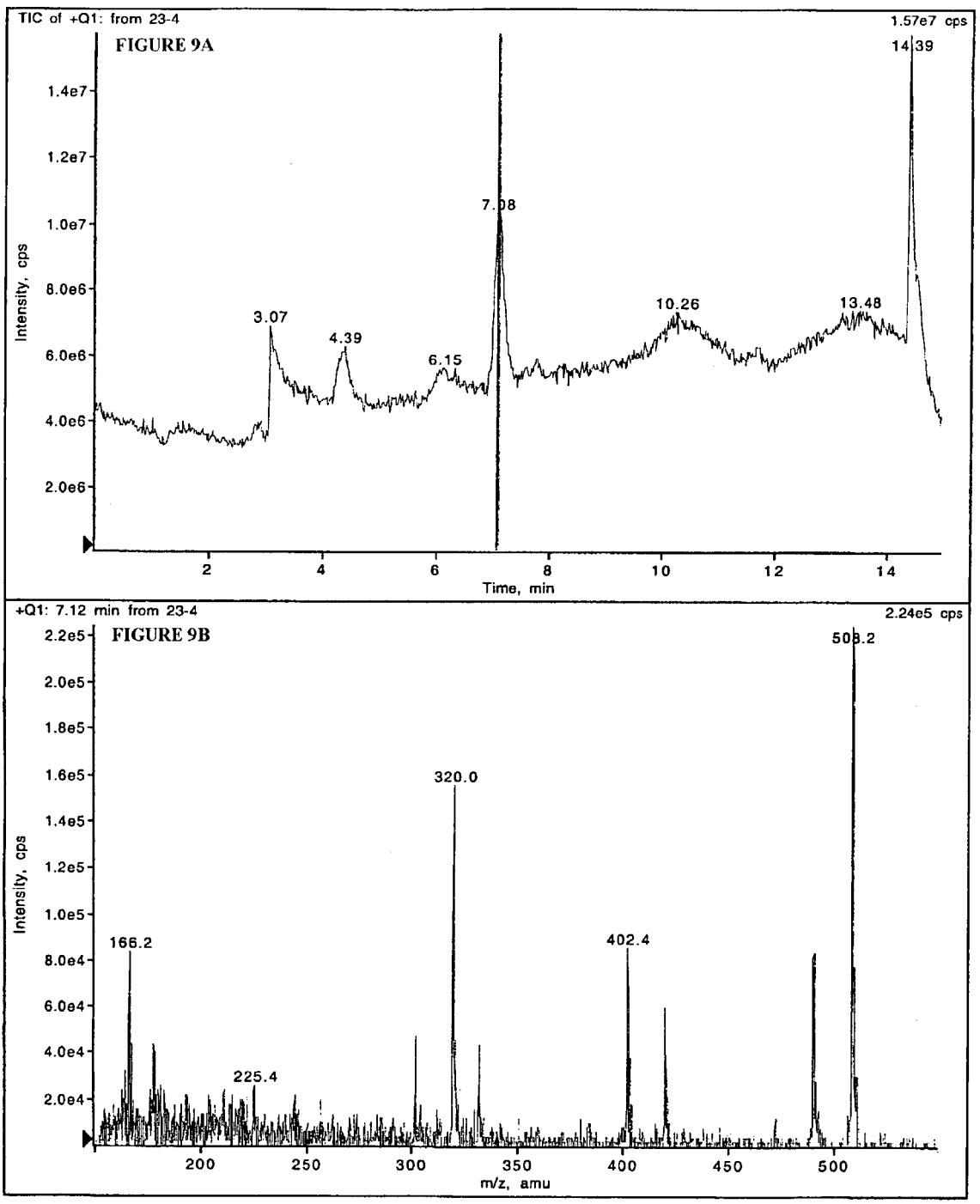

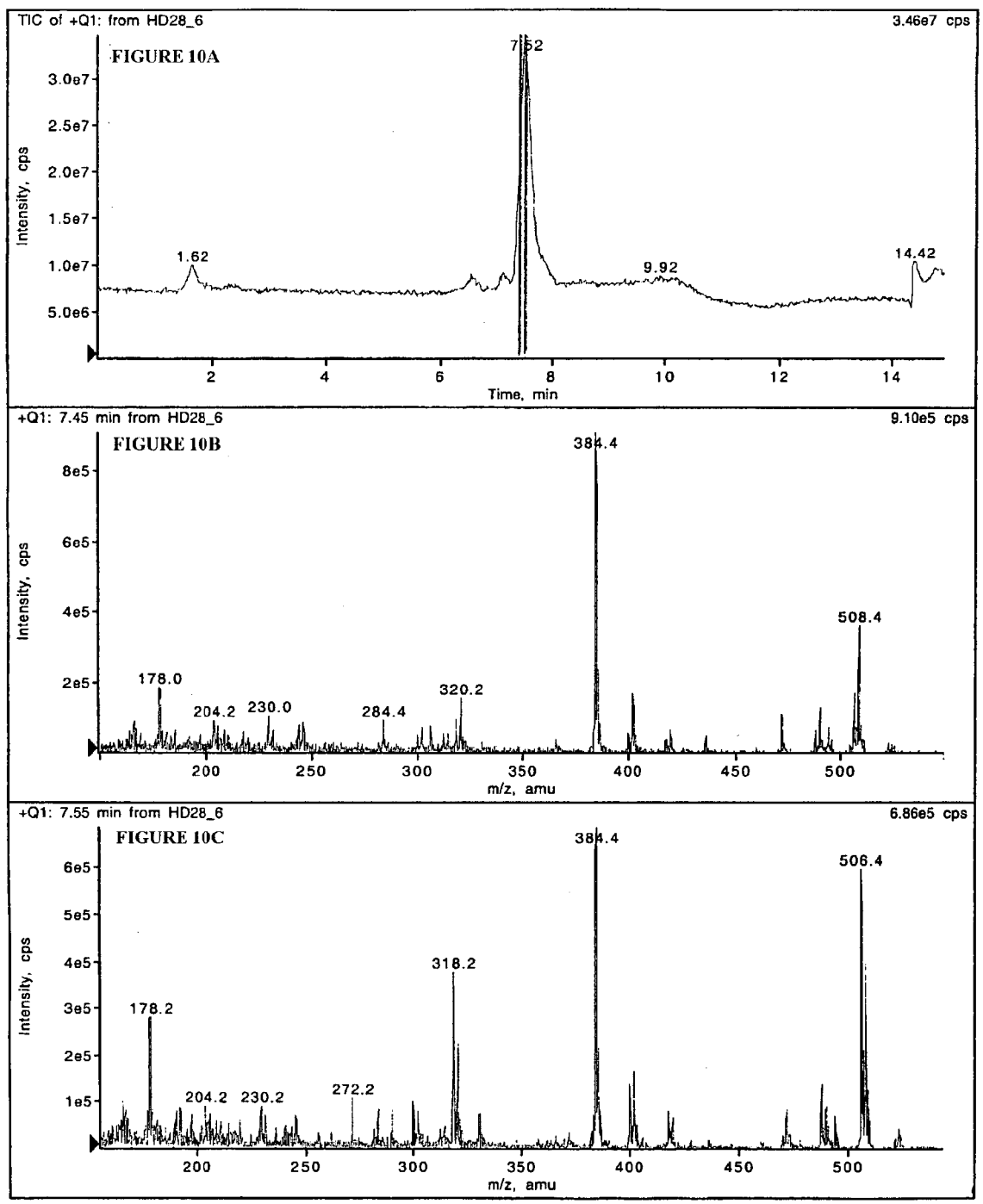

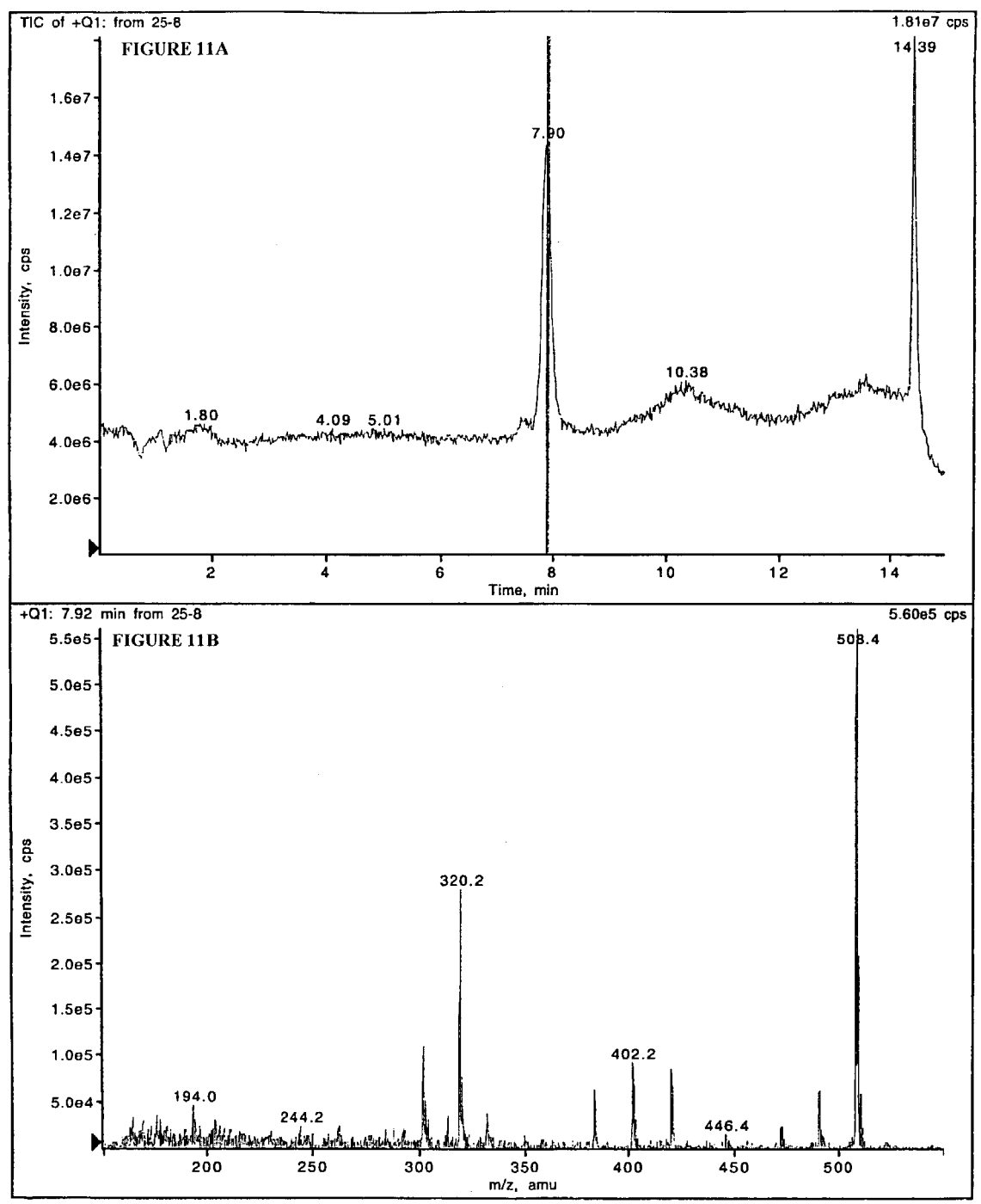

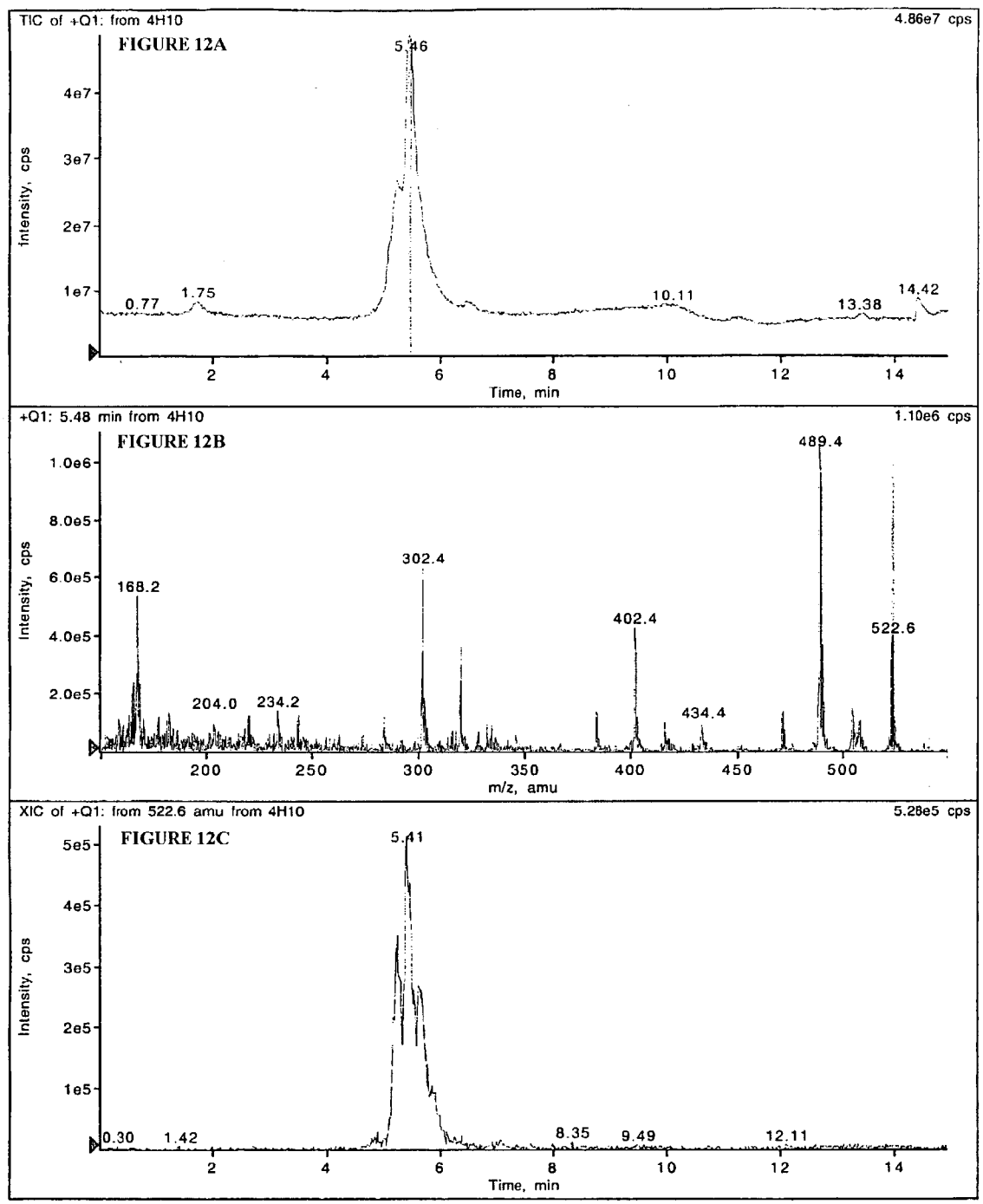

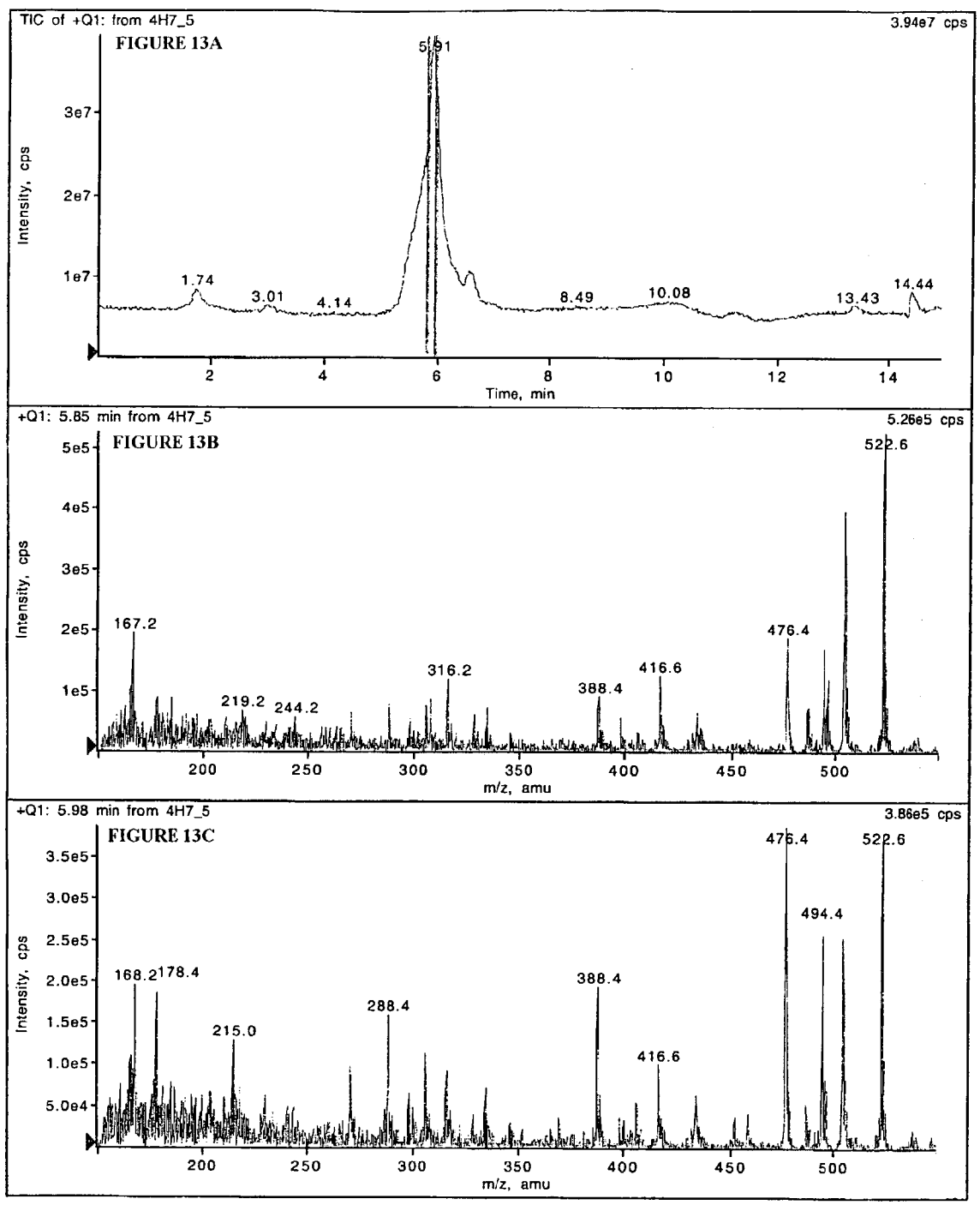

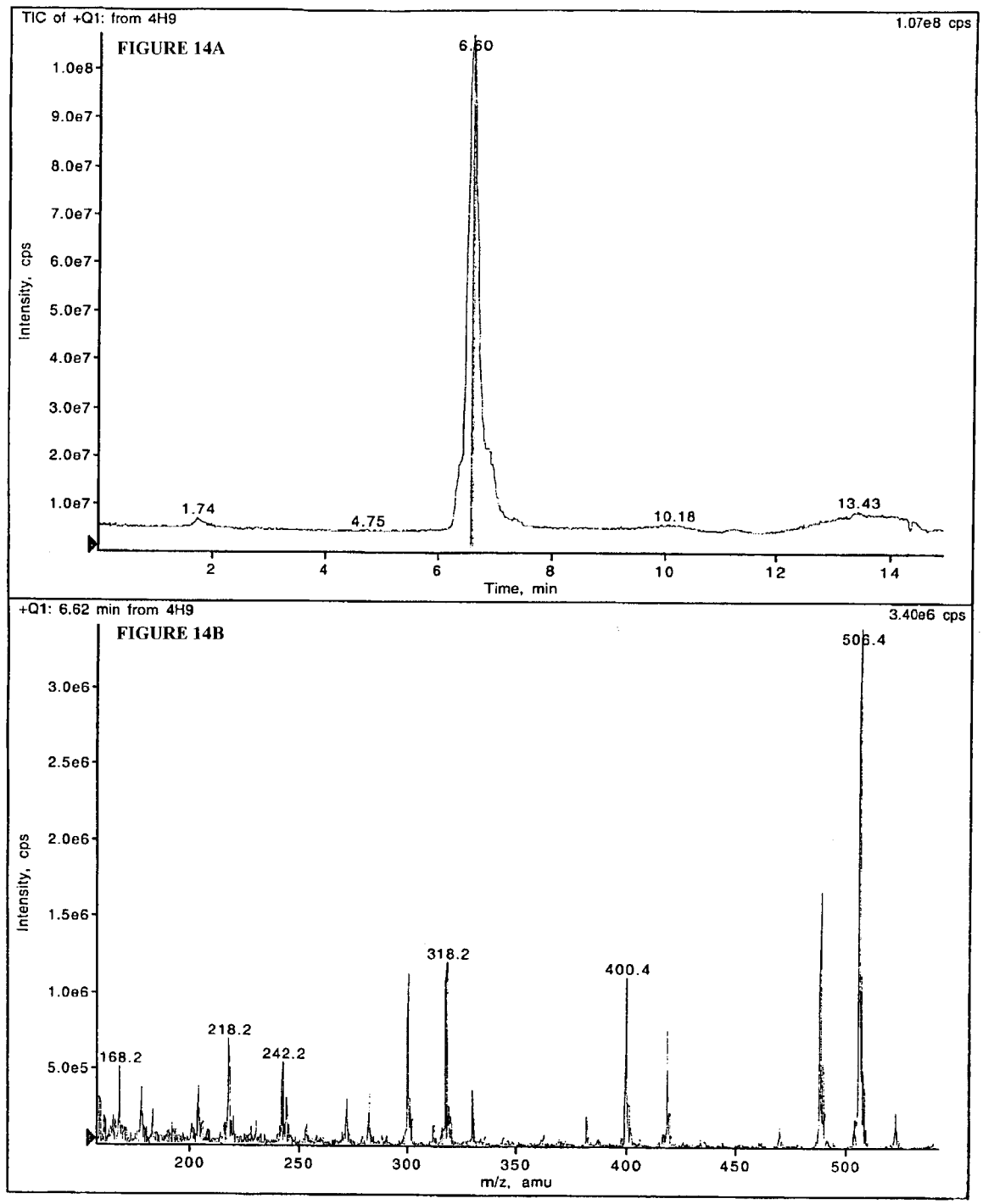

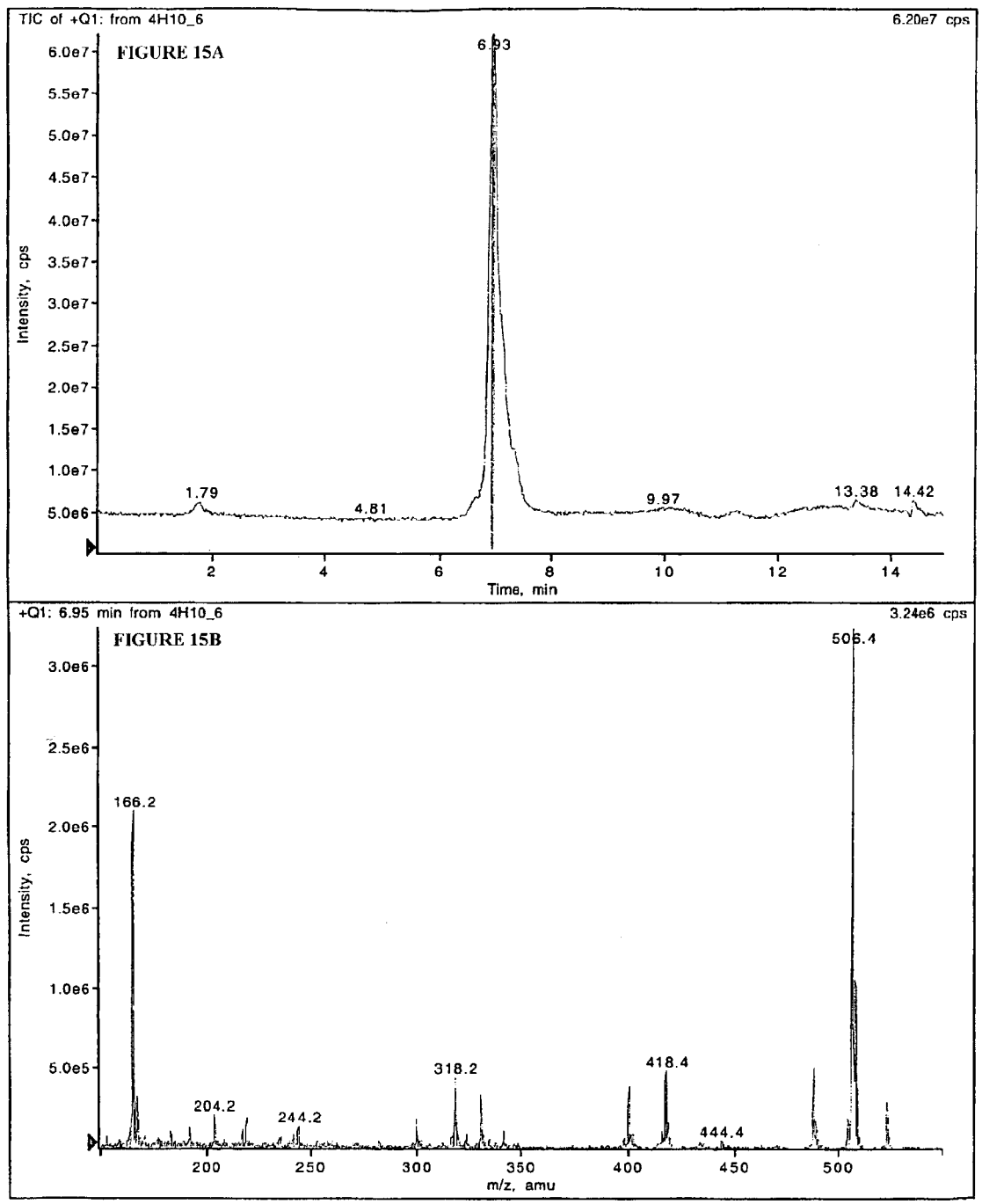

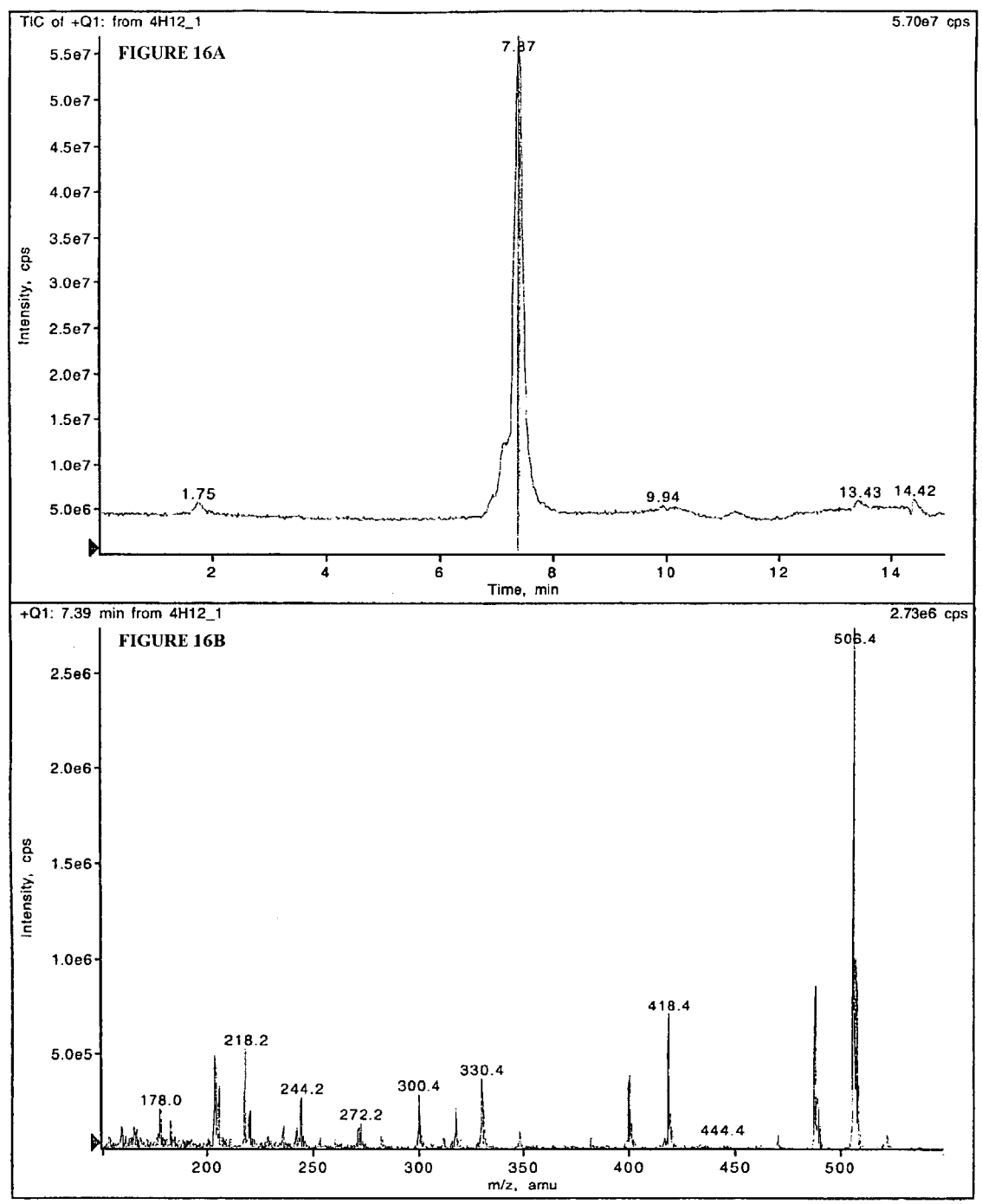

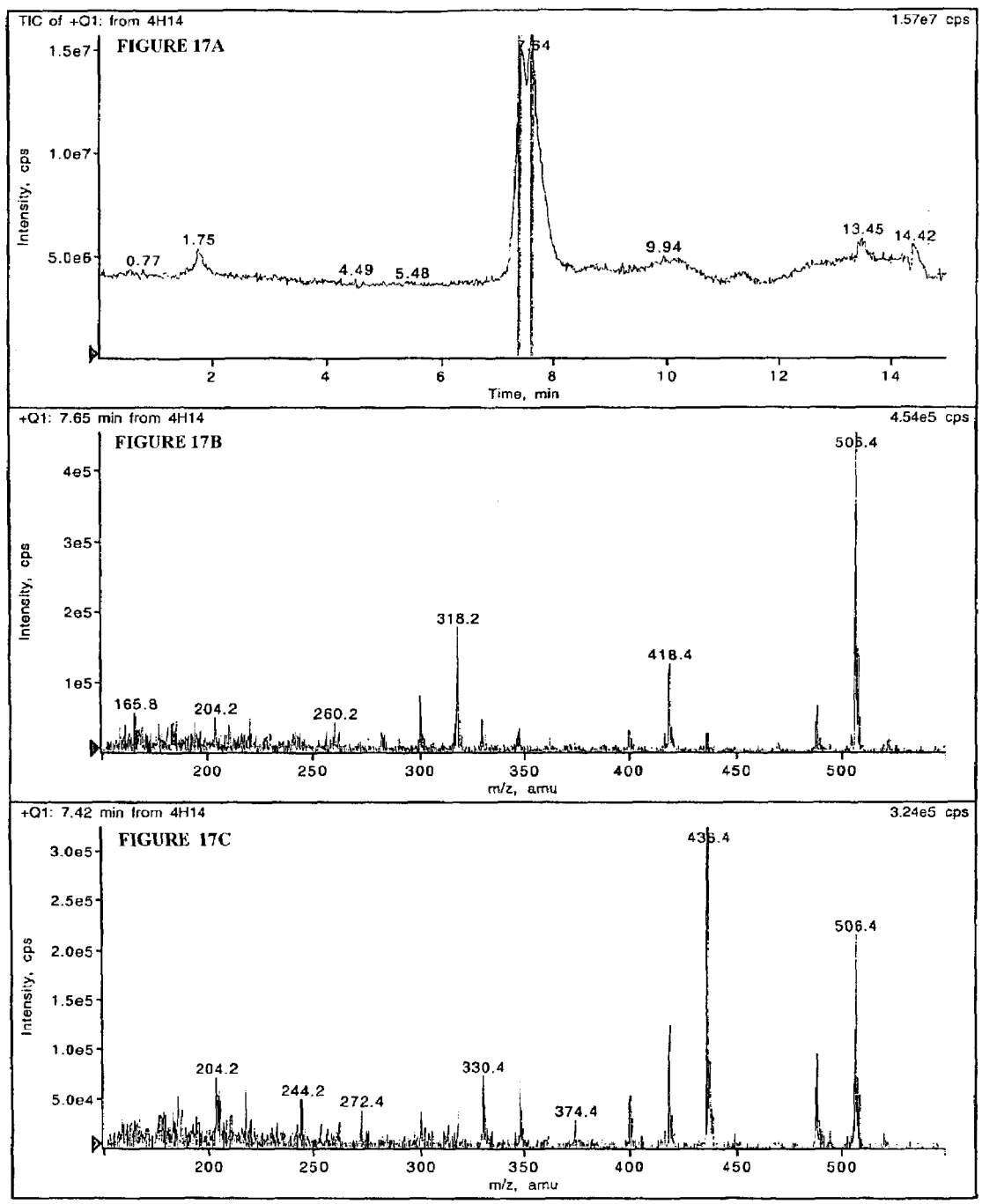

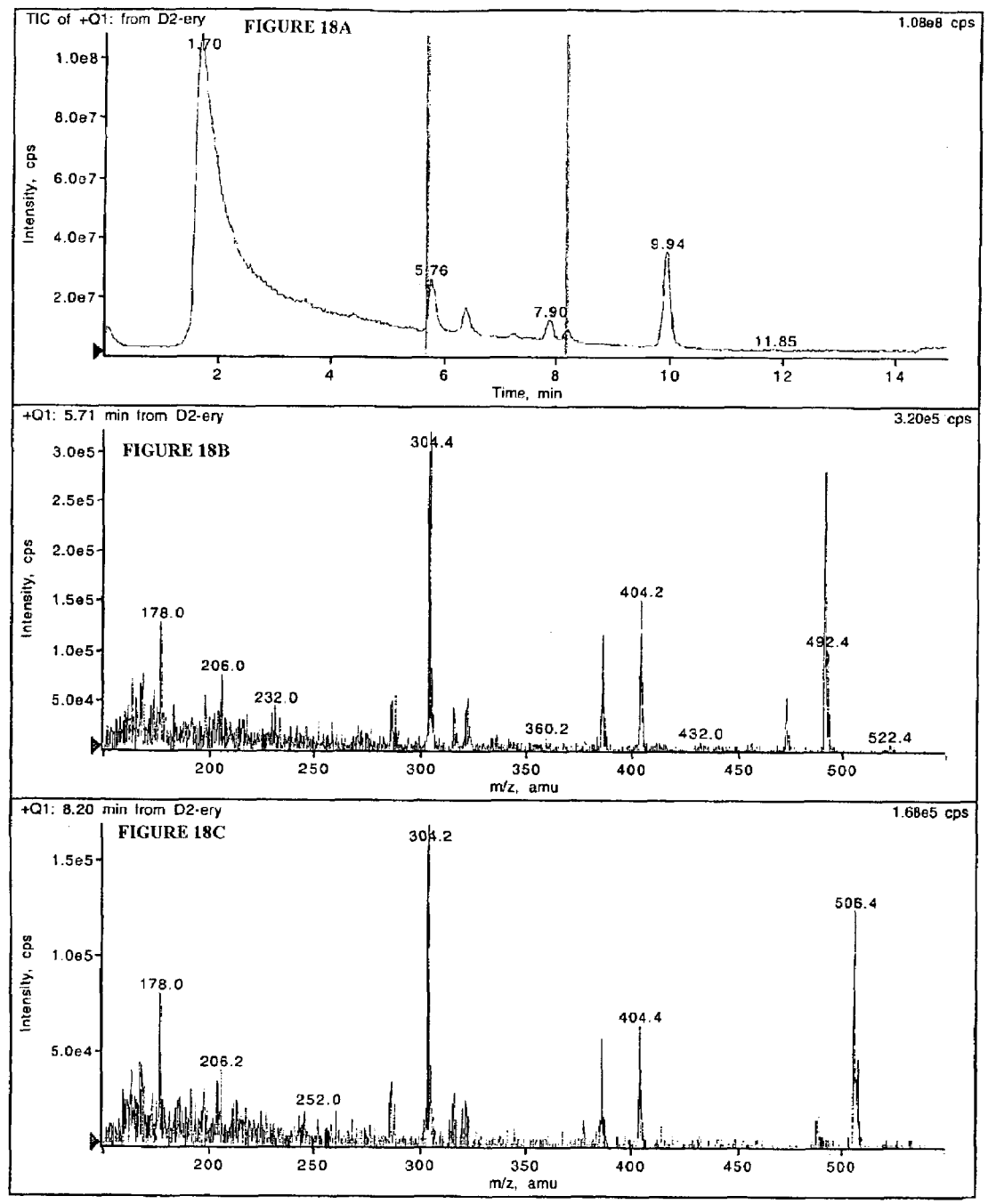

EPOTHILONE COMPOUNDS AND METHODS FOR MAKING THE SAME

Figures 8A, 8B:
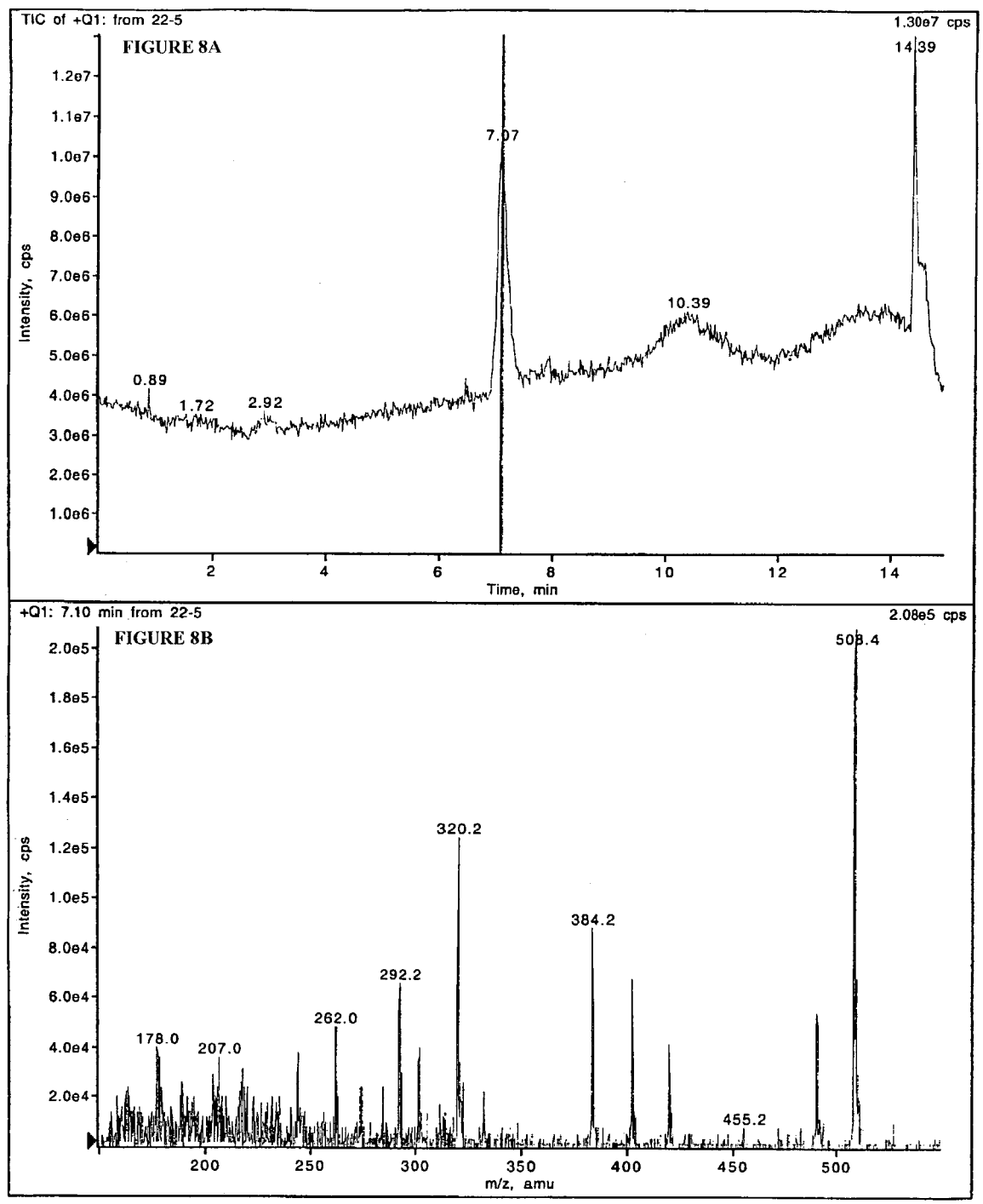

This application claims the benefit of U.S. Provisional Application No. 60/334,734, filed Nov. 15, 2001.

BACKGROUND

Epothilone A (R═H) and Epothilone B (R═$CH_3$) are produced by *Sorangium cellulosum* strain So ce 90, the structures of which are shown below, and were the first of several epothilones to be isolated and characterized. Höfle et al., 1996, *Angew. Chem. Int. Ed. Engl.* 35(13/14): 1567–1569.

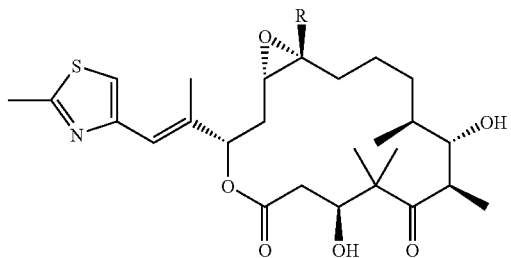

Epothilone A and epothilone B possess many of the advantageous properties of taxol. As a result, there is significant interest in these and structurally related compounds as potential chemotherapeutic agents. The desoxy counterparts of epothilones A and B are known as epothilone C (R═H) and epothilone D (R═$CH_3$), and also exhibit similar anti-tumor activity but with less cytotoxicity. The structures of epothilones C and D are shown below.

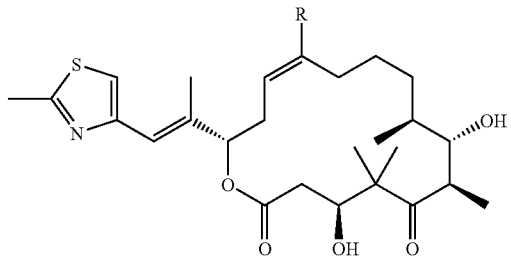

Other epothilone compounds have since been described. These include other naturally occurring epothilones such as the 39 compounds isolated from *Sorangium cellulosum* So ce 90 of which epothilones A, B, C, and D together account for approximately 98.9% of the total epothilones produced (WO 99/65913) and epothilone analogs derived from de novo chemical synthesis (see e.g., WO 98/25929; WO 99/01124; WO 99/02514; WO 99/07692; WO 99/43653;WO 99/54319; WO 99/67253; WO 00/37473; WO 00/50423; and WO 00/66589). Epothilone compounds derived from bioconversion also have been disclosed. For example, PCT publication WO 00/39276 describes the use of *Amycolata autotrophica* ATCC 35203 to convert epothilone B to epothilone F (which differs from epothilone B by the addition of a hydroxyl at C-21).

Due to the increasing interest in epothilones as anti-cancer agents, novel derivatives of these compounds are needed and desired to more fully develop their therapeutic potential.

DESCRIPTION OF THE PREFERRED EMBODIMENTS

PCT publication WO 00/39276 discloses the bioconversion of epothilone B to epothilone F using *Amycolata autotrophica* ATCC 35203 or *Actinomyces* sp. strain SC15847 PTA-1043.

The present invention relates to the unexpected finding that bioconversion methods can be used to alter the oxidation state of a generic epothilone compound in addition to the conversion of epothilone B into epothilone F that was disclosed by WO 00/39276.

In one embodiment, a microorganism that possess a hydroxylase or an epoxidase or other P450 enzyme is used to alter the oxidation state of an epothilone compound by bioconversion, with the proviso that when the microorganism is *Amycolata autotrophica* ATCC 35203 or *Actinomyces* sp. strain SC15847 PTA-1043 and the epothilone compound is epothilone B that the oxidation of C-21 to a C-21 hydroxyl to yield epothilone F is excluded. In another embodiment, the microorganism is *Saccharopolyspora erythrea*. In another embodiment, the microorganism is *Saccharopolyspora erythrea* NRRL 2338. In another embodiment, the microorganism is *Saccharopolyspora erythrea* K39-14, a mutant strain of *Saccharopolyspora erythrea* Italy strain that has an inactivating mutation in the ketosynthase domain in module 1 of the erythronolide polyketide synthase so that 6-deoxyerythronolide is not produced. In another embodiment, the microorganism is *Streptomyces hygroscopicus* ATCC 55098.

In another embodiment, the hydroxylase or epoxidase is purified using methods known in the art from the bioconverting microorganism, and the purified enzyme is used to alter the oxidation state of the epothilone compound. In another embodiment, the gene for the hydroxylase or epoxidase from the bioconverting microorganism is cloned and expressed in a non-native host cell (with respect to the hydroxylase or epoxidase) that also expresses the gene for the epothilone PKS such that the host makes the epothilone compound (whose oxidation state has been altered) directly. Methods for the expression of an epothilone PKS in host cells are disclosed in PCT Publications WO 00/31247 and WO 01/83800 which are incorporated herein by reference.

In another embodiment, the microorganism *Amycolata autotrophica* ATCC 35203 is used to alter the oxidation date of an epothilone compound with the proviso that when the epothilone compound is epothilone B, that the oxidation at C-21 to epothilone F is excluded. In one embodiment, the method adds a hydroxyl group to an epothilone compound at a position other that at C-21. In another embodiment, the method adds at least two hydroxyl groups. In another embodiment, the method adds an epoxide to a double bond of an epothilone compound. In another embodiment, the method adds an epoxide to the C-12, C13 double bond of a desoxyepothilone compound. In another embodiment, the method adds a hydroxyl and an epoxide to an epothilone compound.

In another embodiment, *A. autotrophica* ATCC 35203 is used to alter the oxidation state of epothilone D to yield novel epothilone compounds. Example 1A describes this method in greater detail. The use of *A. autotrophica* to bioconvert epothilone D yields 14 compounds, many of which are novel compounds of the present invention. These compounds include: 8 derivatives that differ from epothilone D by +16 mass units; 2 derivatives that differ from epothilone D by +32 mass units; 1 derivatives that differs from epothilone D by +48 mass units; and 1 derivative that differ from epothilone D by +14 mass units. Derivatives that differ by +16 mass units either have been established to differ or are postulated to differ from epothilone D by the addition of a hydroxyl or an epoxide. Derivatives that differ by +32 mass units either have been established to differ or are postulated to differ from epothilone D by the addition of two hydroxyls, two epoxides, or a hydroxyl and an epoxide. The derivative that differs by +48 mass units is postulated to differ from epothilone D by the addition of either (i) three hydroxyls; (ii) two hydroxyls and an epoxide; or (iii) one hydroxyl and two epoxides. The derivative that differs by +14 mass units is postulated to differ from epothilone D by the conversion of a —CH$_2$— into —C(=O)—, although the addition of a methyl group is also a possibility. FIGS. 1–11 are LC/MS spectra for these derivatives. Where the structure of the epothilone derivative has been identified, it is so noted in the following discussions.

FIG. 1A is the total ion chromatogram of an epothilone D derivative that elutes at approximately 4.51 minutes under the HPLC conditions described in Example 2. FIG. 1B is the mass spectrum of this compound. This compound differs from epothilone D by the addition of 32 mass units.

FIG. 2A is the total ion chromatogram of an epothilone D derivative that elutes at approximately 4.80 minutes under the HPLC conditions described in Example 2. FIG. 2B is the mass spectrum of this compound. This compound differs from epothilone D by the addition 32 mass units and has been identified as 21, 26-dihydroxy epothilone D. Example 25 describes the analytical data for 21,26-dihydroxyepothilone D.

FIG. 3A is the total ion chromatogram of an epothilone D derivative that elutes at approximately 5.40 minutes under the HPLC conditions described in Example 2. FIG. 3B is the mass spectrum of this compound. This compound differs from epothilone D by the addition of 48 mass units.

FIG. 4A is the total ion chromatogram of an epothilone D derivative that elutes at approximately 5.88 minutes under the HPLC conditions described in Example 2. FIG. 4B is the mass spectrum of this compound. This compound differs from epothilone D by the addition of 16 mass units and has been identified as 14-hydroxyepothilone D. Example 26 describes the analytical data for 14-hydroxyepothilone D.

FIG. 5A is the total ion chromatogram of an epothilone D derivative that elutes at approximately 6.10 minutes under the HPLC conditions described in Example 2. FIG. 5B is the mass spectrum of this compound. This compound differs from epothilone D by the addition of 16 mass units and has been identified as 11-hydroxy epothilone D. Example 3 describes the analytical data for 11-hydroxy epothilone D.

FIG. 6A is the total ion chromatogram of an epothilone D derivative that elutes at approximately 6.30 minutes under the HPLC conditions described in Example 2. FIG. 6B is the mass spectrum of this compound. This compound differs from epothilone D by the addition of 16 mass units and has been identified as 26-hydroxy epothilone D. Example 27 describes the analytical data for 26-hydroxyepothilone D.

FIG. 7A is the total ion chromatogram of an epothilone D derivative that elutes at approximately 6.92 minutes under the HPLC conditions described in Example 2. FIG. 6 B is the mass spectrum of this compound. This compound differs from epothilone D by the addition of 16 mass units.

FIG. 8A is the total ion chromatogram of an epothilone D derivative that elutes at approximately 7.07 minutes under the HPLC conditions described in Example 2. FIG. 8B is the mass spectrum of this compound. This compound differs from epothilone D by the addition of 16 mass units and has been identified as 9-hydroxy epothilone D. Example 28 describes the analytical data for 9-hydroxyepothilone D.

FIG. 9A is the total ion chromatogram of an epothilone D derivative that elutes at approximately 7.08 minutes under the HPLC conditions described in Example 2. FIG. 9B is the mass spectrum of this compound. This compound differs from epothilone D by the addition of 16 mass units and has been identified as epothilone B (which differs from epothilone D by the addition of an epoxide at the C-12 and C-13 double bond).

FIG. 10A is the total ion chromatogram of two epothilone derivatives that co-elute at approximately 7.52 minutes under the HPLC conditions described in Example 2. FIG. 10B is the mass spectrum of one of the compounds and differs from epothilone D by the addition of 16 mass units. FIG. 10C is the mass spectrum of the other compound and differs from epothilone D by 14 mass units.

FIG. 11A is the total ion chromatogram of an epothilone D derivative that elutes at approximately 7.90 minutes under the HPLC conditions described in Example 2. FIG. 11B is the mass spectrum of this compound. This compound differs from epothilone D by the addition of 16 mass units and has been identified as 21-hydroxy epothilone D. Example 29 describes the analytical data for 21-hydroxyepothilone D.

In another embodiment, *A. autotrophica* ATCC 35203 is used to alter the oxidation state of epothilone 490 to yield several novel epothilone compounds. The method is similar to that described in Example 1 for epothilone D except that epothilone 490 is used instead of epothilone D. The structure of epothilone 490 is shown below.

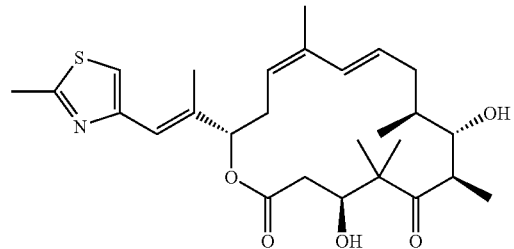

Epothilone 490 differs from epothilone D by the presence of a second double bond at C-10 and C-11, and was previously described by U.S. Ser. No. 09/825,876 filed Apr. 3, 2001 entitled EPOTHILONE COMPOUNDS AND METHODS FOR MAKING AND USING THE SAME by inventors Robert Arslanian, John Carney and Brian Metcalf which is incorporated herein by reference. The use of *A. autotrophica* to bioconvert epothilone 490 yields novel compounds of the present invention. These compounds include: 5 derivatives that differ from epothilone 490 by +16 mass units and 3 derivatives that differ from epothilone 490 by +32 mass units. Derivatives that differ by +16 mass units either have been established to differ or are postulated to differ from epothilone 490 by the addition of a hydroxyl or an epoxide. Derivatives that differ by +32 mass units either have been established to differ or are postulated to differ from epothilone 490 by either (i) the addition of two hydroxyls; (ii) the addition of two epoxides; (iii) or the addition of one hydroxyl and one epoxide. FIGS. 12–17 are LC/MS spectra for these derivatives. Where the epothilone derivative has been identified, it is so noted in the following discussions.

FIG. 12A is the total ion chromatogram of an epothilone 490 derivative that elutes at approximately 5.46 minutes under the HPLC conditions described in Example 2. FIG. 12B is the mass spectrum of this compound. This compound differs from epothilone 490 by the addition of 32 mass units. FIG. 12C is the identification of the elution peak (at 5.41 minutes) that corresponds to mass 522.6 in FIG. 12B.

FIG. 13A is the total ion chromatogram of two epothilone 490 derivatives that co-elute at approximately 5.91 minutes under the HPLC conditions described in Example 2. FIG. 13B is the mass spectrum of one of these compounds and differs from epothilone 490 by the addition of 32 mass units. FIG. 13C is the mass spectrum of the other compound and also differs from epothilone 490 by the addition of two hydroxyl groups.

FIG. 14A is the total ion chromatogram of an epothilone 490 derivative that elutes at approximately 6.60 minutes under the HPLC conditions described in Example 2. FIG. 14B is the mass spectrum of this compound and differs from epothilone 490 by the addition of 16 mass units. This compound has been identified as 26-hydroxy epothilone 490. Example 30 describes the analytical data for 26-hydroxyepothilone 490.

FIG. 15A is the total ion chromatogram of an epothilone 490 derivative that elutes at approximately 6.93 minutes under the HPLC conditions described in Example 2. FIG. 15B is the mass spectrum of this compound and differs from epothilone 490 by the addition of 16 mass units.

FIG. 16A is the total ion chromatogram of an epothilone 490 derivative that elutes at approximately 7.37 minutes under the HPLC conditions described in Example 2. FIG. 16B is the mass spectrum of this compound and differs from epothilone 490 by the addition of 16 mass units.

FIG. 17A is the total ion chromatogram of two epothilone 490 derivatives that co-elute at approximately 7.64 minutes under the HPLC conditions described in Example 2. FIG. 17B is the mass spectrum of one of the compounds and has been identified as 21-hydroxy epothilone 490. FIG. 17C is the mass spectrum of the other compound and differs from epothilone 490 by the addition of 16 mass units. Example 31 describes the analytical data for 21-hydroxyepothilone 490.

In another embodiment, *Saccharopolyspora erythrea* K39-14 is used to alter the oxidation state of epothilone D. Example 1B describes this method in greater detail. This method yields two hydroxylated compounds that were identified as 21-hydroxy epothilone D and 26-hydroxy epothilone D and two compounds which LC/MS spectra are shown in FIGS. 18A–18C. FIG. 18A is the total ion chromatogram of the latter two epothilone derivatives, one eluting at approximately 5.76 minutes and the other eluting at approximately 8.20 minutes under the HPLC conditions described in Example 2. Under these conditions, 21-hydroxy epothilone D elutes at approximately 7.90 minutes and 26-hydroxy epothilone D elutes at approximately 6.3 minutes. FIG. 18B is the mass spectrum of the compound that elutes at approximately 5.71 minutes. This compound differs from epothilone D by the addition of 16 mass units. FIG. 18C is the mass spectrum of the compound that elutes at approximately 8.20 minutes and differs from epothilone D by the addition of 14 mass units. The derivative that differs by +16 mass units is postulated to differ from epothilone D by the addition of a hydroxyl or an epoxide. The derivative that differs by +14 mass units is postulated to differ from epothilone D by the conversion of a —CH$_2$— into —C(=O)—, although the addition of a methyl group is also a possibility.

In another aspect of the present invention, methods are provided for adding to an epothilone compound a hydroxyl group at C-26 or C-21, or C-11 or C-9, or any combination thereof, provided that when the microorganism is *Amycolata autotrophica* ATCC 35203 or *Actinomyces* sp. strain SC15847 PTA-1043 and the epothilone compound is epothilone B, that the addition of a hydroxyl at C-21 to yield epothilone F is excluded. The method comprises contacting an epothilone compound with a microorganism that expresses a hydroxylase.

In one embodiment, there is provided a method of adding to an epothilone compound a hydroxyl group at C-14 or C-21 by contacting a *Streptomyces hygroscopicus* ATCC 55098 microorganism producing a hydroxylase with an epothilone compound, provided that when the epothilone compound is epothilone B, that the addition of a hydroxyl at C-21 to yield epothilone F is excluded. In one embodiment, the epothilone compound is epothilone D. In one embodiment the microorganism producing a hydroxylase is *Streptomyces hygroscopicus* ATCC 55098.

In one embodiment, the microorganism is *A. autotrophica* ATCC 35203 and is used to convert a compound of the structure

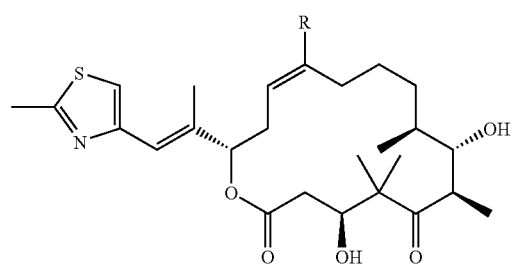

to a compound of the structure

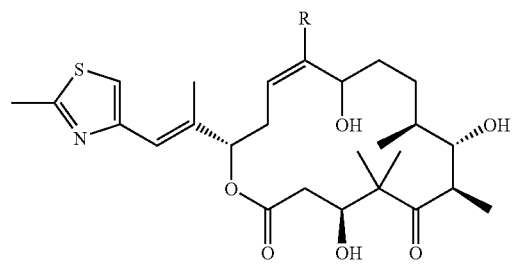

wherein R is hydrogen or methyl . In another embodiment, the method is used to convert a compound of the structure

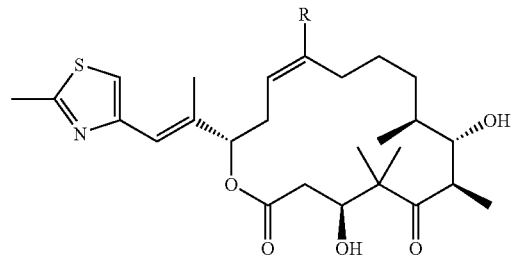

to a compound of the structure

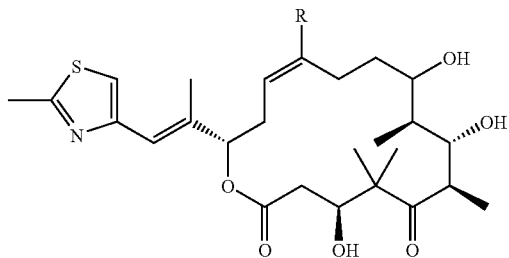

wherein R is hydrogen or methyl. In another embodiment, the method is used to convert a compound of the structure

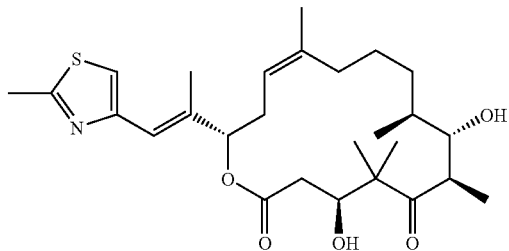

to a compound of the structure

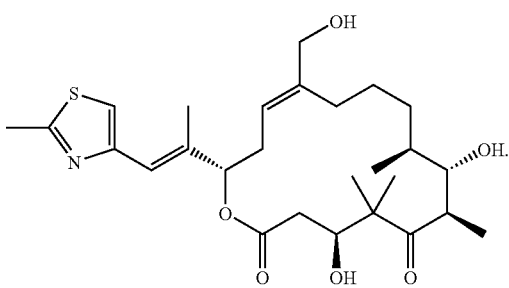

In another aspect of the invention, methods are provided for adding an epoxide at the C-12, C-13 double bond of a desoxyepothilone. The method comprises contacting a desoxyepothilone a microorganism that expresses an epoxidase.

In one embodiment, the microorganism is *A. autotrophica* ATCC 35203 and is used to convert a compound of the structure

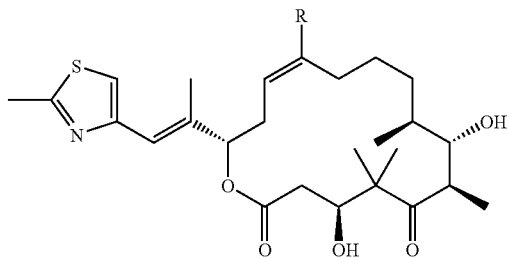

to a compound of the structure

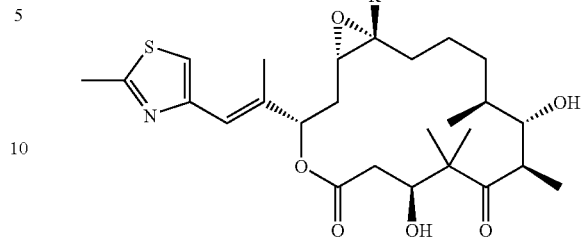

wherein R is hydrogen or methyl.

In one embodiment, the microorganism is *Streptomyces hygroscopicus* ATCC 55098 and is used to convert a compound of the structure

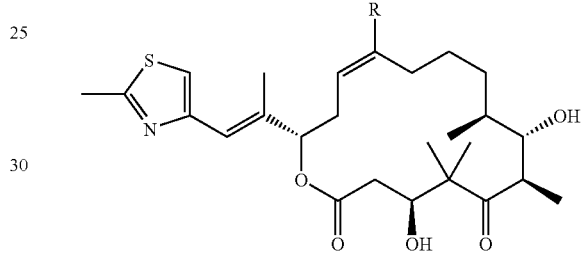

to a compound of the structure

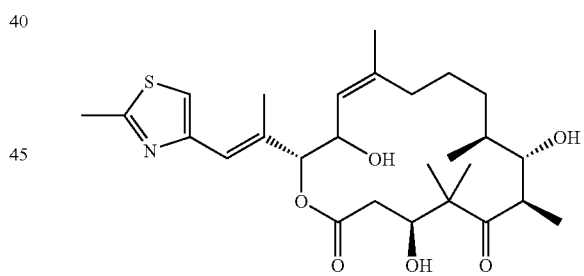

wherein R is hydrogen or methyl.

In one embodiment of the present invention, compounds having the structure

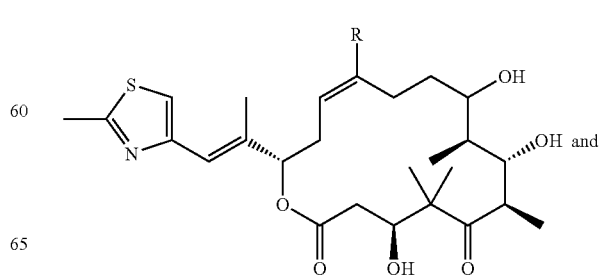

-continued

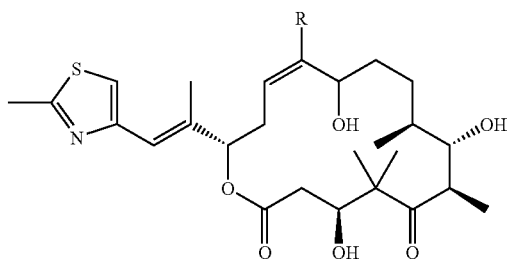

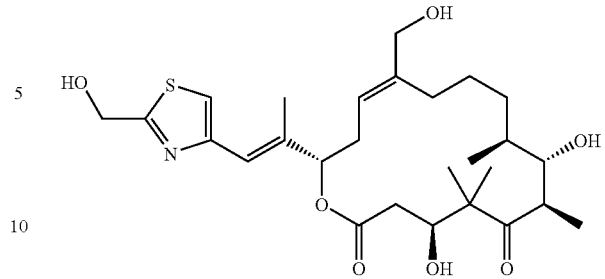

are provided wherein R is hydrogen or methyl. These compounds are obtained from the bioconversion of epothilone C or epothilone D and are useful as anti-cancer agents or as intermediates thereto. In another embodiment of the invention, the compounds having the structures are provided. These compounds are obtained from the bioconversion of epothilone D and are useful as anti-cancer agents or as intermediates thereto.

In another aspect of the present invention, the compounds having the structure

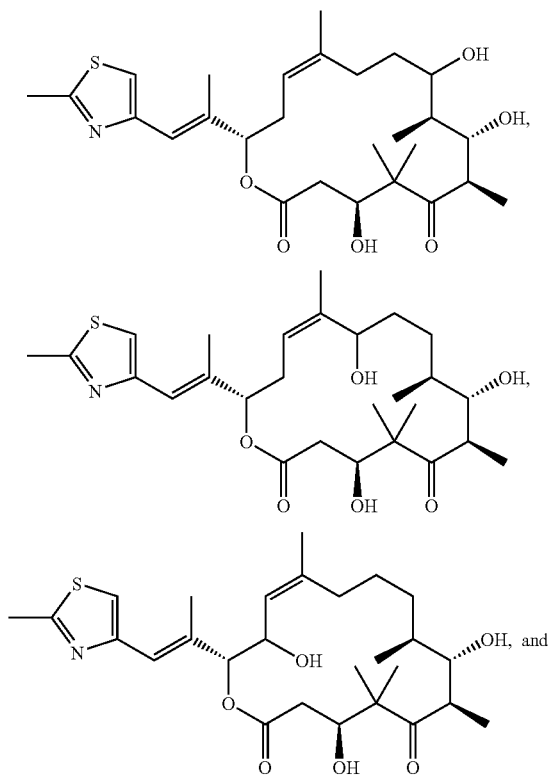

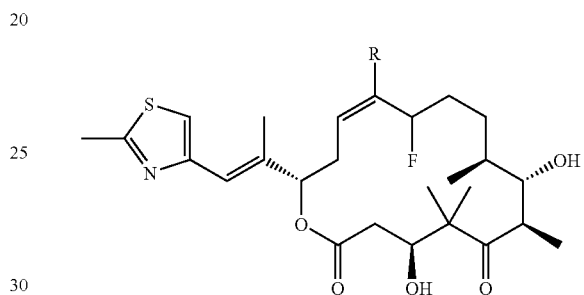

are provided wherein R is hydrogen or methyl. 11-Fluoro epothilone C and 11-fluoro epothilone D are obtained using chemical methods from 11-hydroxy epothilone C and 11-hydroxy epothilone D respectively. 11-Fluoro epothilones C and D are useful as anti-cancer agents or as intermediates thereto.

In another aspect of the present invention, two methods are provided for converting an 11-hydroxy epothilone compound to the 11-fluoro epothilone compound. In the first method, the displacement of the C-11 group with the fluoro occurs with retention of the starting C-11 configuration. In the second method, the displacement of the C-11 group with the fluoro occurs with inversion of the starting C-11 configuration. As a result, regardless of the configuration of the 11-hydroxy epothilone compound, both isomers of the corresponding 11-fluoro epothilone compound can be obtained.

Scheme 1 illustrates the two fluorination methods where the starting material is 11(S)-hydroxy epothilone D.

SCHEME 1

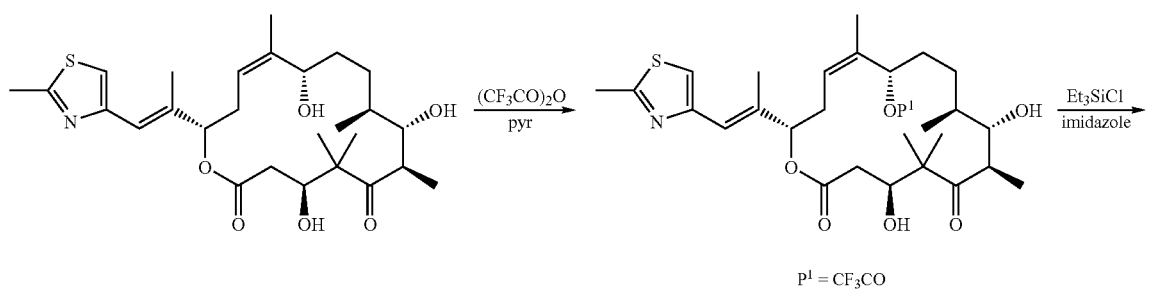

P¹ = CF₃CO

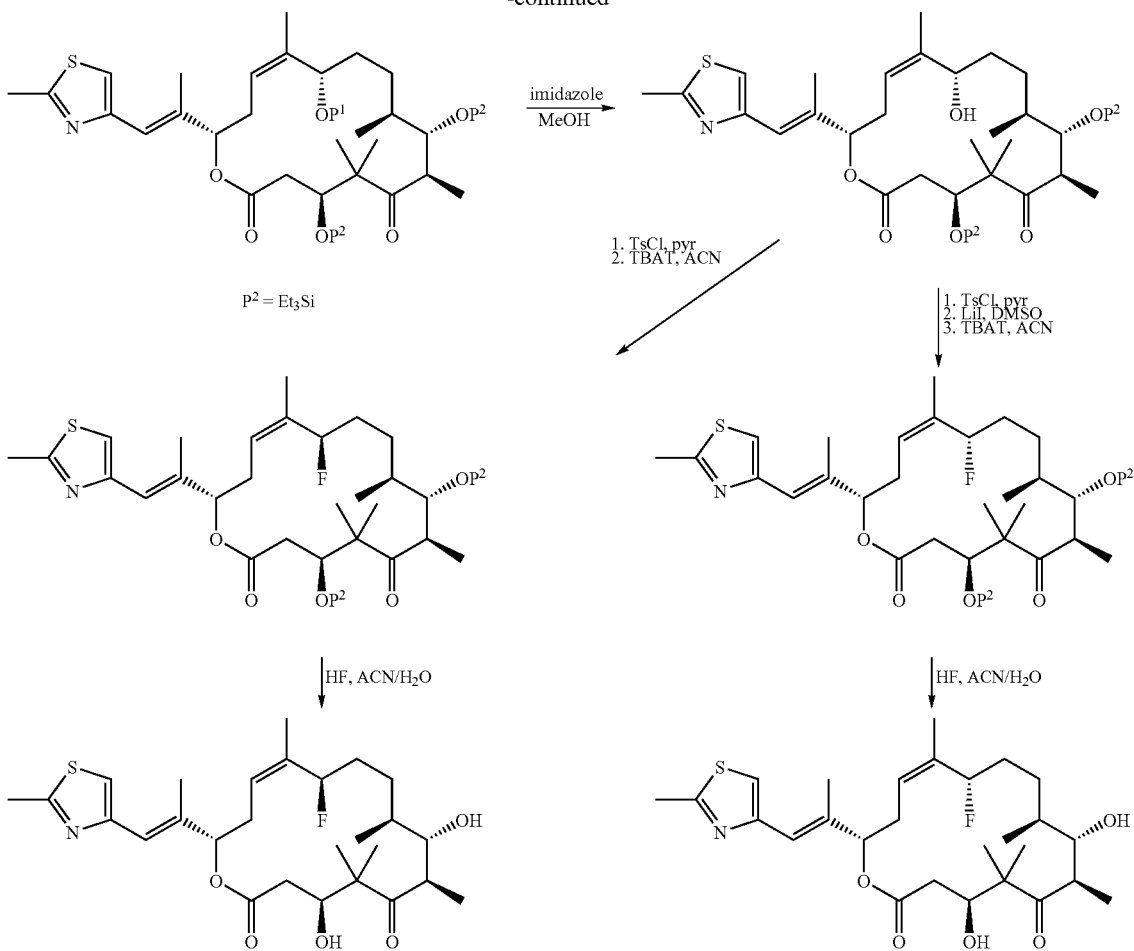

As illustrated by Scheme 1, 11(S)-hydroxy epothilone D is treated with trifluoroacetic anhydride and pyridine to protect the C-11 hydroxyl group (Example 4). The 11(S)-trifluoroacetoxy epothilone D is treated with chlorotriethyl silane and imidazole to protect the C-3 and C-7 hydroxyl groups (Example 5). The 3,7-bis(O-triethylsilyl)-11(S)-trifluoroacetoxy epothilone D is then treated with methanol and imidazole to selectively deprotect the C-11 hydroxyl group (Example 6). Reaction of 3,7-bis(O-triethylsilyl)11(S)-hydroxy epothilone D with p-toluenesulfonyl chloride and pyridine and then tetrabutylammonium triphenyldifluorosilicate in anhydrous acetonitrile yields 3,7-bis(O-triethylsilyl)-11(R)-fluoro epothilone D (Examples 7–8) which is deprotected to the desired product, 11(R)-fluoro epothilone D (Example 9).

Alternatively, 3,7-bis(O-triethylsilyl)-11(S)-hydroxy epothilone D is treated with p-toluenesulfonyl chloride and pyridine; lithium iodide in anhydrous methylsulfoxide; and tetrabutylammonium triphenyldifluorosilicate in anhydrous acetonitrile to yield 3,7-bis(O-triethylsilyl)-11(S)-fluoro epothilone D (Examples 4, 10–11). Deprotection yields the desired product, 11(S)-fluoro epothilone D (Example 12).

Scheme 2 illustrates the two fluorination methods where the starting material is 11(R)-hydroxy epothilone D.

SCHEME 2

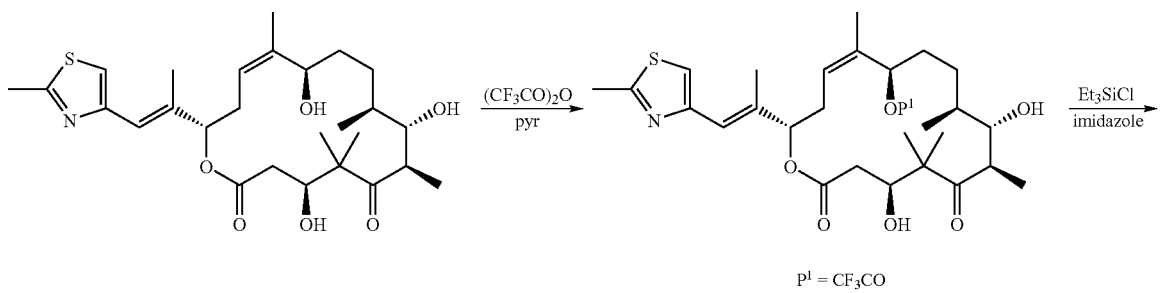

$P^1 = CF_3CO$

-continued

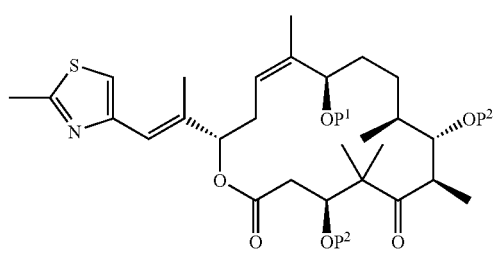

P² = Et₃Si

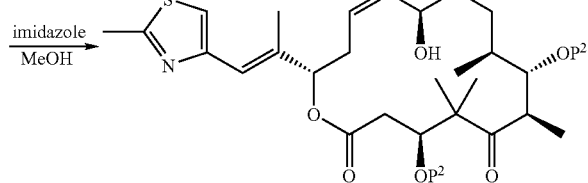

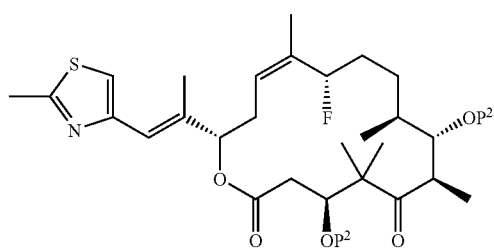

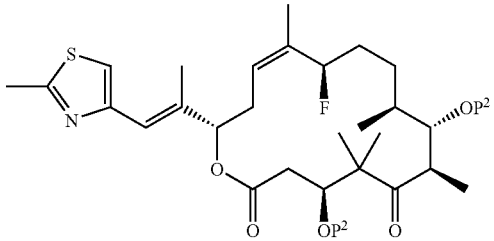

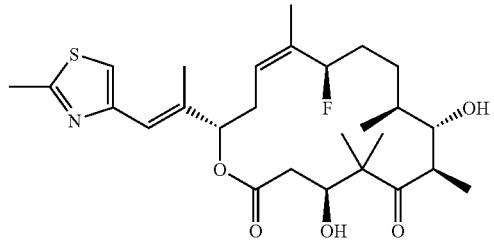

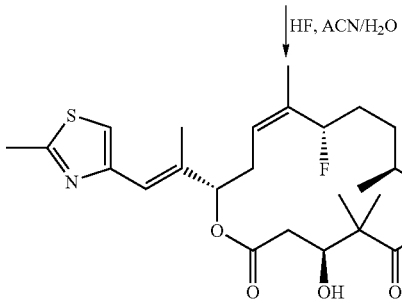

As illustrated by Scheme 2, 11(R)-hydroxy epothilone D is treated with trifluoroacetic anhydride and pyridine to protect the C-11 hydroxyl group (Example 13). The 11(R)-trifluoroacetoxy epothilone D is treated with chlorotriethyl silane and imidazole to protect the C-3 and C-7 hydroxyl groups (Example 14). The 3,7-bis(O-triethylsilyl)-11(R)-trifluoroacetoxy epothilone D is then treated with methanol and imidazole to selectively deprotect the C-11 hydroxyl group (Example 15). Reaction of 3,7-bis(O-triethylsilyl)-11(R)-hydroxy epothilone D with p-toluenesulfonyl chloride and pyridine and then tetrabutylammonium triphenyldifluorosilicate in anhydrous acetonitrile yields 3,7-bis(O-triethylsilyl)-11(S)-fluoro epothilone D (Examples 16–17) which is deprotected to the desired product, 11(S)-fluoro epothilone D (Example 18).

Alternatively, 3,7-bis(O-triethylsilyl)-11(R)-hydroxy epothilone D is treated with p-toluenesulfonyl chloride and pyridine; lithium iodide in anhydrous methylsulfoxide; and tetrabutylammonium triphenyldifluorosilicate in anhydrous acetonitrile to yield 3,7-bis(O-triethylsilyl)-11(R)-fluoro epothilone D (Examples 16, 19–20). Deprotection yields the desired product, 11(R)-fluoro epothilone D (Example 21).

Formulation

A composition of the present invention generally comprises an inventive compound and a pharmaceutically acceptable carrier. The inventive compound may be free form or where appropriate as pharmaceutically acceptable derivatives such as prodrugs, and salts and esters of the inventive compound.

The composition may be in any suitable form such as solid, semisolid, or liquid form. See Pharmaceutical Dosage Forms and Drug Delivery Systems, 5th edition, Lippicott Williams & Wilkins (1991) which is incorporated herein by reference. In general, the pharmaceutical preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used.

In one embodiment, the compositions containing an inventive compound are Cremophor®-free. Cremophor® (BASF Aktiengesellschaft) is a polyethoxylated castor oil which is typically used as a surfactant in formulating low soluble drugs. However, because Cremophor® can case allergic reactions in a subject, compositions that minimize or eliminate Cremophor® are preferred. Formulations of epothilone A or B that eliminate Cremophor® are described for example by PCT Publication WO 99/39694 which is incorporated herein by reference and may be adapted for use with the inventive compounds.

Where applicable, the inventive compounds may be formulated as microcapsules and nanoparticles. General protocols are described for example, by Microcapsules and Nanoparticles in Medicine and Pharmacy by Max Donbrow, ed., CRC Press (1992) and by U.S. Pat. Nos. 5,510,118; 5,534,270; and 5,662,883 which are all incorporated herein by reference. By increasing the ratio of surface area to volume, these formulations allow for the oral delivery of compounds that would not otherwise be amenable to oral delivery.

The inventive compounds may also be formulated using other methods that have been previously used for low solubility drugs. For example, the compounds may form emulsions with vitamin E or a PEGylated derivative thereof as described by WO 98/30205 and 00/71163 which are incorporated herein by reference. Typically, the inventive compound is dissolved in an aqueous solution containing ethanol (preferably less than 1% w/v). Vitamin E or a PEGylated-vitamin E is added. The ethanol is then removed to form a pre-emulsion that can be formulated for intravenous or oral routes of administration. Another strategy involves encapsulating the inventive compounds in liposomes. Methods for forming liposomes as drug delivery vehicles are well known in the art. Suitable protocols include those described by U.S. Pat. Nos. 5,683,715 ; 5,415,869, and 5,424,073 which are incorporated herein by reference relating to another relatively low solubility cancer drug taxol and by PCT Publication WO 01/10412 which is incorporated herein by reference relating to epothilone B. Of the various lipids that may be used, particularly preferred lipids for making epothilone-encapsulated liposomes include phosphatidylcholine and polyethyleneglycol-derivitized distearyl phosphatidylethanolamine. Example 22 provides an illustrative protocol for making liposomes containing 11-fluoro-epothilone D, the general method which can be readily adapted to make liposomes containing other compounds of the present invention.

Yet another method involves formulating the inventive compounds using polymers such as polymers such as biopolymers or biocompatible (synthetic or naturally occurring) polymers. Biocompatible polymers can be categorized as biodegradable and non-biodegradable. Biodegradable polymers degrade in vivo as a function of chemical composition, method of manufacture, and implant structure. Illustrative examples of synthetic polymers include polyanhydrides, polyhydroxyacids such as polylactic acid, polyglycolic acids and copolymers thereof, polyesters polyamides polyorthoesters and some polyphosphazenes. Illustrative examples of naturally occurring polymers include proteins and polysaccharides such as collagen, hyaluronic acid, albumin, and gelatin.

Another method involves conjugating the compounds of the present invention to a polymer that enhances aqueous solubility. Examples of suitable polymers include polyethylene glycol, poly-(d-glutamic acid), poly-(l-glutamic acid), poly-(l-glutamic acid), poly-(d-aspartic acid), poly-(l-aspartic acid), poly-(l-aspartic acid) and copolymers thereof. Polyglutamic acids having molecular weights between about 5,000 to about 100,000 are preferred, with molecular weights between about 20,000 and 80,000 being more preferred and with molecular weights between about 30,000 and 60,000 being most preferred. The polymer is conjugated via an ester linkage to one or more hydroxyls of an inventive epothilone using a protocol as essentially described by U.S. Pat. No. 5,977,163 which is incorporated herein by reference. Preferred conjugation sites include the hydroxyl off carbon-21 in the case of 21-hydroxy-derivatives of the present invention. Other conjugation sites include the hydroxyl off carbon 3, the hydroxyl off carbon 7 and where applicable, the hydroxyl off carbon 11.

In another method, the inventive compounds are conjugated to a monoclonal antibody. This strategy allows the targeting of the inventive compounds to specific targets. General protocols for the design and use of conjugated antibodies are described in Monoclonal Antibody-Based Therapy of Cancer by Michael L. Grossbard, ed. (1998) which is incorporated herein by reference.

The amount of active ingredient that may be combined with the carrier materials to produce a single dosage form will vary depending upon the subject treated and the particular mode of administration. For example, a formulation for intravenous use comprises an amount of the inventive compound ranging from about 1 mg/mL to about 25 mg/mL, preferably from about 5 mg/mL to 15 mg/ML, and more preferably about 10 mg/mL. Intravenous formulations are typically diluted between about 2 fold and about 30 fold with normal saline or 5% dextrose solution prior to use.

Methods to Treat Cancer

In one aspect of the present invention, the inventive compounds are used to treat cancer. In one embodiment, the compounds of the present invention are used to treat cancers of the head and neck which include tumors of the head, neck, nasal cavity, paranasal sinuses, nasopharynx, oral cavity, oropharynx, larynx, hypopharynx, salivary glands, and paragangliomas. In another embodiment, the compounds of the present invention are used to treat cancers of the liver and biliary tree, particularly hepatocellular carcinoma. In another embodiment, the compounds of the present invention are used to treat intestinal cancers, particularly colorectal cancer. In another embodiment, the compounds of the present invention are used to treat ovarian cancer. In another embodiment, the compounds of the present invention are used to treat small cell and non-small cell lung cancer. In another embodiment, the compounds of the present invention are used to treat breast cancer. In another embodiment, the compounds of the present invention are used to treat sarcomas which includes fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma. In another embodiment, the compounds of the present invention are used to treat neoplasms of the central nervous systems, particularly brain cancer. In another embodiment, the compounds of the present invention are used to treat lymphomas which include Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma.

The method comprises administering a therapeutically effective amount of an inventive compound to a subject suffering from cancer. The method may be repeated as necessary either to contain (i.e. prevent further growth) or to eliminate the cancer. Clinically, practice of the method will result in a reduction in the size or number of the cancerous growth and/or a reduction in associated symptoms (where applicable). Pathologically, practice of the method will produce at least one of the following: inhibition of cancer cell proliferation, reduction in the size of the cancer or tumor, prevention of further metastasis, and inhibition of tumor angiogenesis.

The compounds and compositions of the present invention can be used in combination therapies. In other words, the inventive compounds and compositions can be administered concurrently with, prior to, or subsequent to one or more other desired therapeutic or medical procedures. The particular combination of therapies and procedures in the combination regimen will take into account compatibility of the therapies and/or procedures and the desired therapeutic effect to be achieved.

In one embodiment, the compounds and compositions of the present invention are used in combination with another anti-cancer agent or procedure. Illustrative examples of other anti-cancer agents include but are not limited to: (i) alkylating drugs such as mechlorethamine, chlorambucil, Cyclophosphamide, Melphalan, Ifosfamide; (ii) antimetabolites such as methotrexate; (iii) microtubule stabilizing agents such as vinblastin, paclitaxel, docetaxel, and discodermolide; (iv) angiogenesis inhibitors; (v) and cytotoxic antibiotics such as doxorubicon (adriamycin), bleomycin, and mitomycin. Illustrative examples of other anti-cancer procedures include: (i) surgery; (ii) radiotherapy; and (iii) photodynamic therapy.

In another embodiment, the compounds and compositions of the present invention are used in combination with an agent or procedure to mitigate potential side effects from the inventive compound or composition such as diarrhea, nausea and vomiting. Diarrhea may be treated with antidiarrheal agents such as opioids (e.g. codeine, diphenoxylate, difenoxin, and loeramide), bismuth subsalicylate, and octreotide. Nausea and vomiting may be treated with antiemetic agents such as dexamethasone, metoclopramide, diphenyhydramine, lorazepam, ondansetron, prochlorperazine, thiethylperazine, and dronabinol. For those compositions that includes polyethoxylated castor oil such as Cremophor®, pretreatment with corticosteroids such as dexamethasone and methylprednisolone and/or $H_1$ antagonists such as diphenylhydramine HCl and/or $H_2$ antagonists may be used to mitigate anaphylaxis. Illustrative formulations for intravenous use and pretreatment regiments are described by Examples 23 and 24 respectively.

Methods of Treating of Non-cancer, Cellular Hyperproliferative Disorders

In another aspect of the present invention, the inventive compounds are used to treat non-cancer disorders that are characterized by cellular hyperproliferation. Illustrative examples of such disorders include but are not limited to: atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, sclerodelma, eczema (including atopic dermatitis. irritant dermatitis, allergic dermatitis), periodontal disease (i.e., periodontitis), polycystic kidney disease, and type I diabetes.

Other examples include vasculitis (e.g., Giant cell arteritis (temporal arteritis, Takayasu's arteritis), polyarteritis nodosa, allergic anguitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic).

The method of treating such diseases comprises administering a therapeutically effective amount of an inventive compound to a subject suffering therefrom. The method may be repeated as necessary. The inventive methods are described in greater detail below with reference to three illustrative non-cancer disorders.

In one embodiment, the compounds of the present invention are used to treat psoriasis, a condition characterized by the cellular hyperproliferation of keratinocytes which builds up on the skin to form elevated, scaly lesions. The method comprises administering a therapeutically effective amount of an inventive compound to a subject suffering from psoriasis. The method may be repeated as necessary either to decrease the number or severity of lesions or to eliminate the lesions. Clinically, practice of the method will result in a reduction in the size or number of skin lesions, diminution of cutaneous symptoms (pain, burning and bleeding of the affected skin) and/or a reduction in associated symptoms (e.g., joint redness, heat, swelling, diarrhea. abdominal pain). Pathologically, practice of the method will result in at least one of the following: inhibition of keratinocyte proliferation, reduction of skin inflammation (for example, by impacting on: attraction and growth factors, antigen presentation, production of reactive oxygen species and matrix metalloproteinases), and inhibition of dermal angiogenesis.

In another embodiment, the compounds of the present invention are used to treat multiple sclerosis, a condition characterized by progressive demyelination in the brain. Although the exact mechanisms involved in the loss of myelin are not understood, there is an increase in astrocyte proliferation and accumulation in the areas of myelin destruction. At these sites, there is macrophage-like activity and increased protease activity which is at least partially responsible for degradation of the myelin sheath. The method comprises administering a therapeutically effective amount of an inventive compound to a subject suffering from multiple sclerosis. The method may be repeated as necessary to inhibit astrocyte proliferation and/or lessen the severity of the loss of motor function and/or prevent or attenuate chronic progression of the disease. Clinically, practice of the method will result in improvement in visual symptoms (visual loss, diplopia), gait disorders (weakness, axial instability, sensory loss, spasticity, hyperreflexia, loss of dexterity), upper extremity dysfunction (weakness, spasticity, sensory loss), bladder dysfunction (urgency, incontinence, hesitancy, incomplete emptying), depression, emotional lability, and cognitive impairment. Pathologically, practice of the method will result in the reduction of one or more of the following, such as myelin loss, breakdown of the blood-brain barrier, perivascular infiltration of mononuclear cells, immunologic abnormalities, gliotic scar formation and astrocyte proliferation, metalloproteinase production, and impaired conduction velocity.

In another embodiment, the compounds of the present invention are used to treat rheumatoid arthritis, a multisystem chronic, relapsing, inflammatory disease that sometimes leads to destruction and ankyiosis of affected joints. Rheumatoid arthritis is characterized by a marked thickening of the synovial membrane which forms villous projections that extend into the joint space, multilayering of the synoviocyte lining (synoviocyte proliferation), infiltration of the synovial membrane with white blood cells (macrophages, lymphocytes, plasma cells, and lymphoid follicles; called an "inflammatory synovitis"), and deposition of fibrin with cellular necrosis within the synovium. The tissue formed as a result of this process is called pannus and, eventually the pannus grows to fill the joint space. The pannus develops an extensive network of new blood vessels through the process of angiogenesis that is essential to the evolution of the synovitis. Release of digestive enzymes (matrix metalloproteinases (e.g., collagenase, stromelysin)) and other mediators of the inflammatory process (e.g., hydrogen peroxide, superoxides, lysosomal enzymes, and products of arachadonic acid metabolism) from the cells of the pannus tissue leads to the progressive destruction of the cartilage tissue. The pannus invades the articular cartilage leading to erosions and fragmentation of the cartilage tissue. Eventually there is erosion of the subchondral bone with fibrous ankylosis and ultimately bony ankylosis, of the involved joint.

The method comprises administering a therapeutically effective amount of an inventive compound to a subject suffering from rheumatoid arthritis. The method may be repeated as necessary to accomplish to inhibit synoviocyte proliferation and/or lessen the severity of the loss of movement of the affected joints and/or prevent or attenuate chronic progression of the disease. Clinically, practice of the present invention will result in one or more of the following: (i) decrease in the severity of symptoms (pain, swelling and tenderness of affected joints; morning stiffness. weakness, fatigue. anorexia, weight loss); (ii) decrease in the severity of clinical signs of the disease (thickening of the joint capsule. synovial hypertrophy, joint effusion, soft tissue contractures, decreased range of motion, ankylosis and fixed joint deformity); (iii) decrease in the extra-articular manifestations of the disease (rheumatic nodules, vasculitis, pulmonary nodules, interstitial fibrosis, pericarditis, episcleritis, iritis, Felty's syndrome, osteoporosis); (iv) increase in the frequency and duration of disease remission/symptom-free periods; (v) prevention of fixed impairment and disability; and/or (vi) prevention/attenuation of chronic progression of the disease. Pathologically, practice of the present invention will produce at least one of the following: (i) decrease in the inflammatory response; (ii) disruption of the activity of inflammatory cytokines (such as IL-I, TNFa, FGF, VEGF); (iii) inhibition of synoviocyte proliferation; (iv) inhibition of matrix metalloproteinase activity, and/or (v) inhibition of angiogenesis.

In another embodiment, the compounds of the present invention are used to threat atherosclerosis and/or restenosis, particularly in patients whose blockages may be treated with an endovascular stent. Atheroschlerosis is a chronic vascular injury in which some of the normal vascular smooth muscle cells ("VSMC") in the artery wall, which ordinarily control vascular tone regulating blood flow, change their nature and develop "cancer-like" behavior. These VSMC become abnormally proliferative, secreting substances (growth factors, tissue-degradation enzymes and other proteins) which enable them to invade and spread into the inner vessel lining, blocking blood flow and making that vessel abnormally susceptible to being completely blocked by local blood clotting. Restenosis, the recurrence of stenosis or artery stricture after corrective procedures, is an accelerated form of atherosclerosis.

The method comprises coating a therapeutically effective amount of an inventive compound on a stent and delivering the stent to the diseased artery in a subject suffering from atherosclerosis. Methods for coating a stent with a compound are described for example by U.S. Pat. Nos. 6,156, 373 and 6,120, 847. Clinically, practice of the present invention will result in one or more of the following: (i) increased arterial blood flow; (ii) decrease in the severity of clinical signs of the disease; (iii) decrease in the rate of restenosis; or (iv) prevention/attenuation of the chronic progression of atherosclerosis. Pathologically, practice of the present invention will produce at least one of the following at the site of stent implantation: (i) decrease in the inflammatory response, (ii) inhibition of VSMC secretion of matrix metalloproteinases; (iii) inhibition of smooth muscle cell accumulation; and (iv) inhibition of VSMC phenotypic dedifferentiation.

Dosage Levels

In one embodiment, dosage levels that are administered to a subject suffering from cancer or a non-cancer disorder characterized by cellular proliferation are of the order from about 1 mg/m$^2$ to about 200 mg/m$^2$ which may be administered as a bolus (in any suitable route of administration) or a continuous infusion (e.g. 1 hour, 3 hours, 6 hours, 24 hours, 48 hours or 72 hours) every week, every two weeks, or every three weeks as needed. It will be understood, however, that the specific dose level for any particular patient depends on a variety of factors. These factors include the activity of the specific compound employed; the age, body weight, general health, sex, and diet of the subject; the time and route of administration and the rate of excretion of the drug; whether a drug combination is employed in the treatment; and the severity of the condition being treated.

In another embodiment, the dosage levels are from about 10 mg/m$^2$ to about 150 mg/m$^2$, preferably from about 10 to about 75 mg/m$^2$ and more preferably from about 15 mg/m$^2$ to about 50 mg/m$^2$ once every three weeks as needed and as tolerated. In another embodiment, the dosage levels are from about 1 mg to about 150 mg/m$^2$, preferably from about 10 mg/m$^2$ to about 75 mg/m$^2$ and more preferably from about 25 mg/m$^2$ to about 50 mg/m$^2$ once every two weeks as needed and as tolerated. In another embodiment, the dosage levels are from about 1 mg/m$^2$ to about 100 mg/m$^2$, preferably from about 5 mg/m$^2$ to about 50 mg/m$^2$ and more preferably from about 10 mg/m$^2$ to about 25 mg/m$^2$ once every week as needed and as tolerated. In another embodiment, the dosage levels are from about 0.1 to about 25 mg/m$^2$, preferably from about 0.5 to about 15 mg/m$^2$ and more preferably from about 1 mg/m$^2$ to about 10 mg/m$^2$ once daily as needed and tolerated.

A detailed description of the invention having been provided above, the following Examples are given for the purpose of illustrating the present invention and shall not be construed as being a limitation on the scope of the invention or claims.

EXAMPLE 1A

*Amycolata autotrophica*

A frozen vial (2 mL) of *Amycolata autotrophica* ATCC 35203 was used to inoculate a 500 mL flask containing 100 ml of a transformation medium (10 g dextrose; 5 g of polypeptone; 5 g. of yeast extract; 5 g of malt extract; all in 1 liter of deionized water), and allowed to grow at 28° C. and 250 rpm for 24 hours. An aliquot (25 mL) was transferred into another 250 mL flask and 10 mg of epothilone D in ethanol was added. The culture was grown for another two days.

EXAMPLE 1B

*Saccharopolyspora erythrea* K39-14

A frozen vial (2 mL) of *Saccharopolyspora erythrea* K39-14 was used to inoculate a 250 mL flask containing 50 ml of R5 medium (Kieser et al., Practical Streptomyces Genetics, John Innes Foundation (2000)), and allowed to grow at 28° C. and 250 rpm for 24 hours. An aliquot (25 mL) is transferred into another 250 mL flask and 10 mg of epothilone D in ethanol is added. The culture is grown for another two days.

EXAMPLE 1C

*Streptomyces hygroscopicus* ATCC 55098

One milliliter of bacterial strain *S. hygroscopicus* ATCC 55098 frozen cells in 20% (v/v)glycerol was inoculated into 40 mL of FM6-1 medium in a 250-mL baffled Erlenmeyer flask. The FM6-1 medium consisted of 30 g/L whole brewers yeast, 15 g/L corn steep liquor, 1 g/L calcium carbonate, 45 g/L corn starch, 23.8 g/L HEPES, and 20 g/L dextrin (Lo-Dex 5). The medium was titrated to pH 7.0 with NaOH prior to sterilization. The batch culture was incubated at 28° C. and 160 rpm on a rotary shaker with a 2 in. stroke for two days. Four hundred microliters of a concentrated stock solution of epothilone D (10 mg/mL) in 100% DMSO was then added to the *S. hygroscopicus* culture. The final epothilone D concentration in the culture was 100 mg/L, and the final DMSO concentration was 1% (v/v). The cells were allowed to grow at 28° C. for another 5 days. Approximately 40 mg/L of epothilone D was converted to the 14-hydroxy-epothilone D analog at the end of the fermentation.

EXAMPLE 2

Samples are analyzed by LC/MS Mass Spectrometer (API 100 LC Perkin-Elmer Sciex Instruments). The samples are loaded onto a 150×4.6 mm ODS-3 5 micron Inertsil column (MetaChem) in acetonitrile and water (gradient 35%–100% in 10 minutes with a flowrate of 1.0 mL/min) and analyzed at a UV wavelength of 250 nm. The start mass was 150 and the stop mass was 550 with a 0.200 amu step and 0.500 ms dwell time. The state table parameters were :IS=0; NC=3; TEM=350; OR=50; RNG=275; Q0=–10; IQ1=–10.999; ST=–16; RO1=–10.500; DF=–250; CEM=2400; NEB=7; CUR=9; QPE=32768; POL=0; VCM=0; and IPE=32768. Under these conditions, epothilone D elutes at approximately 10.2 minutes and epothilone 490 elutes at approximately 9.6 minutes.

EXAMPLE 3

11-Hydroxyepothilone D Characterization

High-resolution MS measurements for the compound were consistent with a formula of $C_{27}H_{41}NO_6S$ for a mono-hydroxylated epothilone D analogue. $^1H$ and $^{13}C$ chemical shifts were assigned from multiplicity-edited HSQC, gsCOSY, and gsHMBC data, and these data were also used to confirm the structure. An HMBC correlation for a methyl singlet at δ 1.70 (H-26) to carbons resonating at δ 120.9 (C-13), 140.7 (C-12), and a secondary alcohol signal at δ 69.8 placed the additional hydroxyl group at the 11 position.

$^1H$ NMR (400 MHz) and $^{13}C$ NMR (100 MHz) data were recorded in $CDCl_3$ solution at 300 K with a Bruker DRX 400 spectrometer equipped with a QNP z-axis gradient probehead. Chemical shifts in $CDCl_3$ solution were referred to δ 7.26 and 77.0 for $^1H$ and $^{13}C$ spectra, respectively. HRMS spectra were obtained by FIA with manual peak-matching on an Applied Biosystems Mariner TOF spectrometer with a turbo-ionspray source in positive ion mode (spray tip potential, 5500 V; spray chamber temp., 400° C.; nozzle potential, 110 V).

11-Hydroxyepothilone D: HRESITOFMS m/z 508.2703; calcd for $C_{27}H_{42}NO_6S$ $[M+H]^+$, 508.2727.

$^1H$ NMR ($CDCl_3$, 400 MHz) δ 6.97 (s, H-19), 6.56 (s, H-17), 5.28 (t, J=8 Hz, H-13), 5.22 (dd, J=6.0, 3.0 Hz, H-15), 4.74 (t, J=8.0 Hz, H-11), 4.42 (dd, J=11, 2.0 Hz, H-3), 3.75 (dd, J=6.5, 1.0 Hz, H-7), 3.24 (qd, J=7.0, 1.0 Hz, H-6), 2.69 (s, H-21), 2.52 (2H, m, $H_2$-14), 2.44 (dd, J=14.0, 11.0, H-2a), 2.19 (dd, J=14.0, 2.0, H-2b), 2.01 (d, J=1.0 Hz, H-27), 1.90 (m, H-8), 1.72 (m, H-10a), 1.70 (s, H-26), 1.58 (H-10b), 1.55 (m, H-9a), 1.37 (s, H-23), 1.29 (m, H-9b), 1.14 (d, J=7.0, H-24), 1.04 (s, H-22), 1.03 (d, J=7.0, H-25).

$^{13}C$ NMR ($CDCl_3$, 100 MHz) δ 221.1 (C-5), 170.1 (C-1), 165.3 (C-20), 151.5 (C-18), 140.7 (C-12), 138.6 (C-16), 120.9 (C-13), 118.4 (C-17), 115.1 (C-19), 77.7 (C-15), 74.0 (C-7), 71.4 (C-3), 69.8 (C-11), 54.4 (C-4), 40.7 (C-6), 39.9 (C-2), 36.5 (C-8), 31.5 (C-10), 30.6 (C-14), 26.6 (C-9), 22.8 (C-23), 18.8 (C-21), 17.8 (C-26), 16.4 (C-27), 16.3 (C-22), 14.6 (C-25), 11.8 (C-24).

EXAMPLE 4

11(S)-trifluoroacetoxyepothilone D

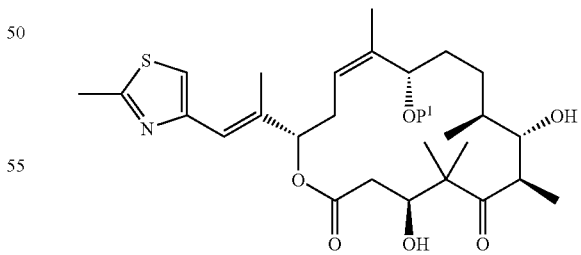

$P^1$ = $CF_3CO$

A solution of 11(S)-hydroxyepothilone D (500 mg) in dry $CH_2Cl_2$ (10 mL) is cooled to 0° C. and treated with trifluoroacetic anhydride (230 mg) and pyridine (79 mg) for 15 minutes. The mixture is evaporated, and the residue is chromatographed on silica gel to provide the product.

EXAMPLE 5

3,7-bis(O-triethylsilyl)-11(S)-trifluoroacetoxyepothilone D

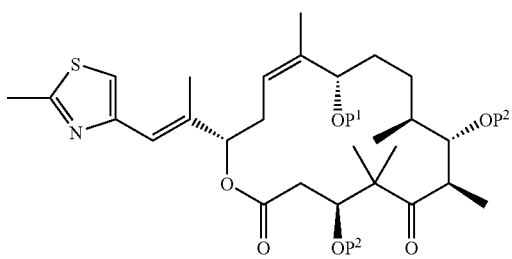

P¹ = CF₃CO
P² = Et₃Si

A solution of 11(S)-trifluoroacetoxyepothilone D (600 mg) in dry $CH_2Cl_2$ (10 mL) is treated with chlorotriethylsilane (350 mg) and imidazole (140 mg) for 12 hours at ambient temperature. The mixture is diluted with $CH_2Cl_2$ and washed sequentially with water and brine, then dried over $MgSO_4$, filtered, and evaporated. The product is purified by chromatography on silica gel.

EXAMPLE 6

3,7-bis(O-triethylsilyl)-11(S)-hydroxyepothilone D

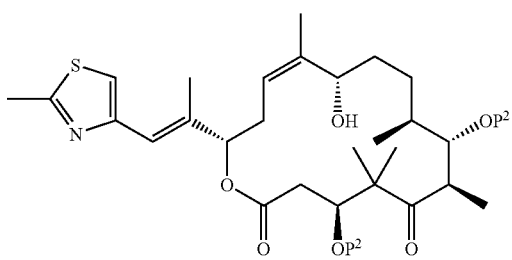

P² = Et₃Si

A solution of 3,7-bis(O-triethylsilyl)-11(S)-trifluoroacetoxyepothilone D (825 mg) in methanol (10 mL) is treated with imidazole (70 mg) for 1 hour. The mixture is evaporated to dryness, and the residue is chromatographed on silica gel.

EXAMPLE 7

3,7-bis(O-triethylsilyl)-11(S)-(p-toluenesulfonyloxy) epothilone D

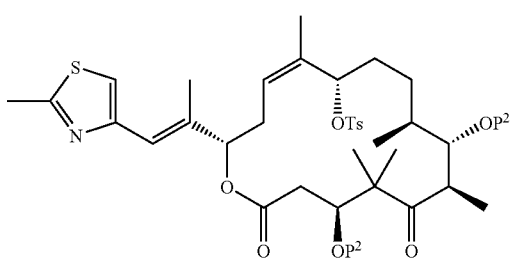

P² = Et₃Si

A solution of 3,7-bis(O-triethylsilyl)-11(S)-hydroxyepothilone D (730 mg) in dry $CH_2Cl_2$ (10 mL) is cooled to 0° C. and treated with p-toluenesulfonyl chloride (200 mg) and pyridine (79 mg). After 1 hour, the mixture is evaporated to dryness. The crude product is used directly without further purification.

EXAMPLE 8

3,7-bis(O-triethylsilyl)-11(R)-fluoroepothilone D

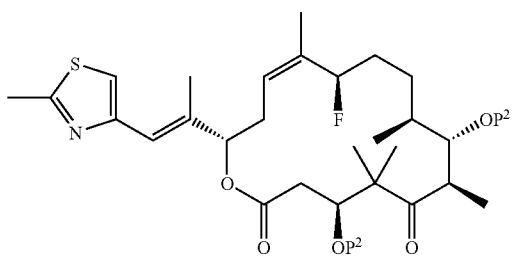

P² = Et₃Si

A solution of the crude 3,7-bis(O-triethylsilyl)-11(S)-(p-toluenesulfonyloxy)epothilone D from Example 7 and tetrabutylammonium triphenyldifluorosilicate (2.0 g) in 25 mL of anhydrous acetonitrile is heated at 70° C. for 1 hour. The mixture is cooled and evaporated. The residue is dissolved in $CH_2Cl_2$ and washed sequentially with water and brine, then dried over $MgSO_4$, filtered, and evaporated. The product is purified by chromatography on silica gel.

EXAMPLE 9

11(R)-fluoroepothilone D

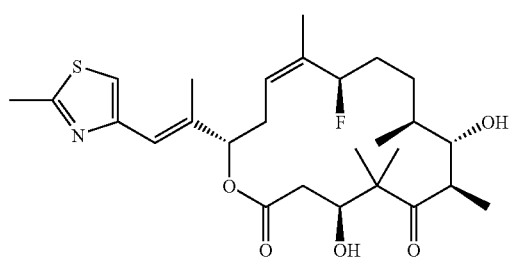

A solution of 3,7-bis(O-triethylsilyl)-11(R)-fluoroepothilone D (750 mg) in 10 mL of 5:1 acetonitrile/water is treated with 48% HF (0.2 mL) for 4 hours at ambient temperature. The mixture is diluted with $CH_2Cl_2$ and washed sequentially with sat. $NaHCO_3$ and brine, then dried over $MgSO_4$, filtered, and evaporated. The product is purified by chromatography on silica gel.

EXAMPLE 10

3,7-bis(O-triethylsilyl)-11(R)-iodoepothilone D

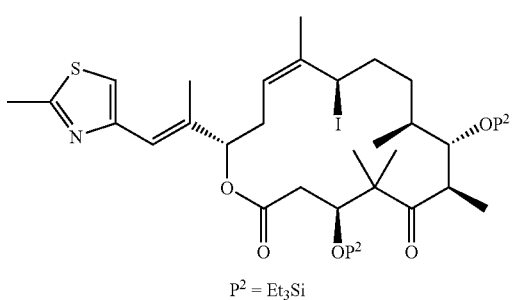

P² = Et₃Si

A solution of the crude 3,7-bis(O-triethylsilyl)-11(S)-(p-toluenesulfonyloxy)epothilone D from Example 4 and lithium iodide (135 mg) in 25 mL of anhydrous methylsulfoxide is heated at 80° C. for 1 hour. The mixture is cooled, dissolved in CH₂Cl₂ and washed sequentially with water and brine, then dried over MgSO₄, filtered, and evaporated. The product is used without further purification.

EXAMPLE 11

3,7-bis(O-triethylsilyl)-11(S)-fluoroepothilone D

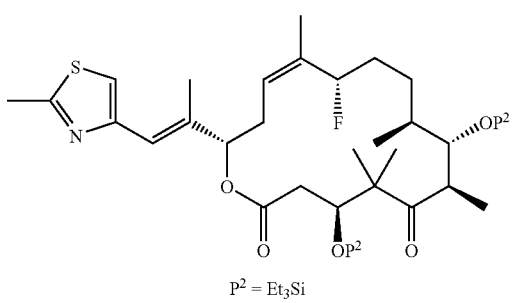

P² = Et₃Si

A solution of the crude protected 11(R)-iodoepothilone from Example 7 and tetrabutylammonium triphenyldifluorosilicate (2.0 g) in 25 mL of anhydrous acetonitrile is heated at 70° C. for 1 hour. The mixture is cooled and evaporated. The residue is dissolved in CH₂Cl₂ and washed sequentially with water and brine, then dried over MgSO₄, filtered, and evaporated. The product is purified by chromatography on silica gel.

EXAMPLE 12

11(S)-fluoroepothilone D

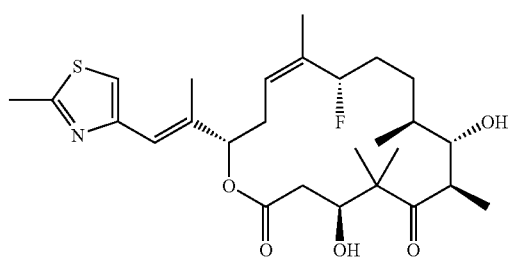

A solution of 3,7-bis(O-triethylsilyl)-11(S)-fluoroepothilone D (750 mg) in 10 mL of 5:1 acetonitrile/water is treated with 48% HF (0.2 mL) for 4 hours at ambient temperature. The mixture is diluted with CH₂Cl₂ and washed sequentially with sat. NaHCO₃ and brine, then dried over MgSO₄, filtered, and evaporated. The product is purified by chromatography on silica gel.

EXAMPLE 13

11(R)-trifluoroacetoxyepothilone D

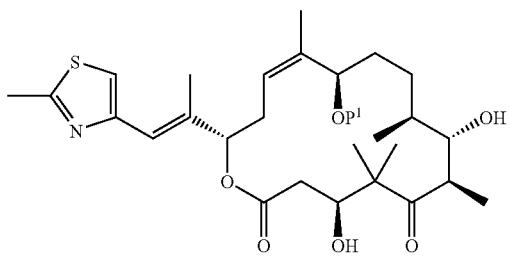

P¹ = CF₃CO

A solution of 11(R)-hydroxyepothilone D (500 mg) in dry CH₂Cl₂ (10 mL) is cooled to 0° C. and treated with trifluoroacetic anhydride (230 mg) and pyridine (79 mg) for 15 minutes. The mixture is evaporated, and the residue is chromatographed on silica gel to provide the product.

EXAMPLE 14

3,7-bis(O-triethylsilyl)-11(R)-trifluoroacetoxyepothilone D

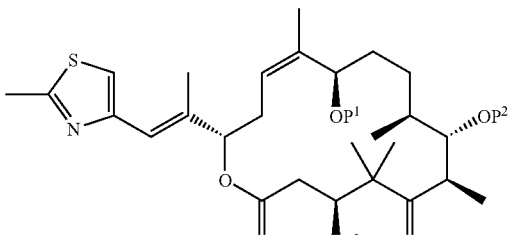

P¹ = CF₃CO
P² = Et₃Si

A solution of 11(R)-trifluoroacetoxyepothilone D (600 mg) in dry CH₂Cl₂ (10 mL) is treated with chlorotriethylsilane (350 mg) and imidazole (140 mg) for 12 hours at ambient temperature. The mixture is diluted with CH₂Cl₂ and washed sequentially with water and brine, then dried over MgSO₄, filtered, and evaporated. The product is purified by chromatography on silica gel.

EXAMPLE 15

3,7-bis(O-triethylsilyl)-11(R)-hydroxyepothilone D

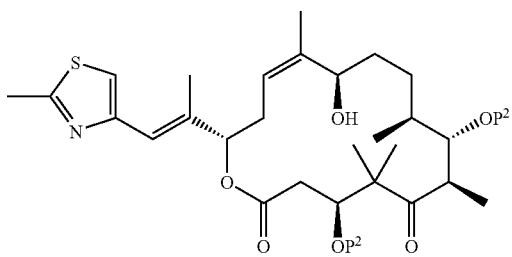

P² = Et₃Si

A solution of 3,7-bis(O-triethylsilyl)-11(R)-trifluoroacetoxyepothilone D (825 mg) in methanol (10 mL) is treated with imidazole (70 mg) for 1 hour. The mixture is evaporated to dryness, and the residue is chromatographed on silica gel.

EXAMPLE 16

3,7-bis(O-triethylsilyl)-11(R)-(p-toluenesulfonyloxy)epothilone D

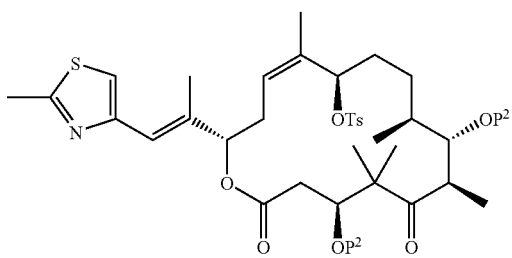

P² = Et₃Si

A solution of 3,7-bis(O-triethylsilyl)-11(R)-hydroxyepothilone D (730 mg) in dry $CH_2Cl_2$ (10 mL) is cooled to 0° C. and treated with p-toluenesulfonyl chloride (200 mg) and pyridine (79 mg). After 1 hour, the mixture is evaporated to dryness. The crude product is used directly without further purification.

EXAMPLE 17

3,7-bis(O-triethylsilyl)-11(S)-fluoroepothilone D

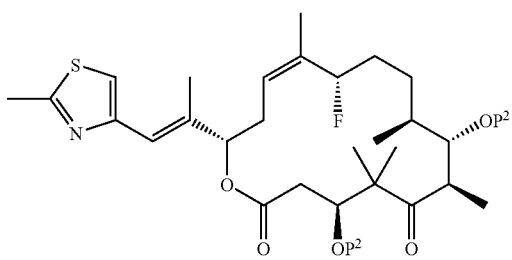

P² = Et₃Si

A solution of the crude 3,7-bis(O-triethylsilyl)-11(R)-(p-toluenesulfonyloxy)epothilone D from Example 16 and tetrabutylammonium triphenyldifluorosilicate (2.0 g) in 25 mL of anhydrous acetonitrile is heated at 70° C. for 1 hour. The mixture is cooled and evaporated. The residue is dissolved in $CH_2Cl_2$ and washed sequentially with water and brine, then dried over $MgSO_4$, filtered, and evaporated. The product is purified by chromatography on silica gel.

EXAMPLE 18

11(S)-fluoroepothilone D

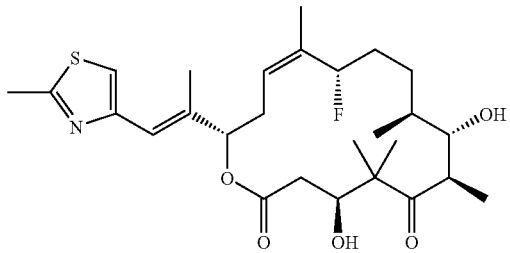

A solution of 3,7-bis(O-triethylsilyl)-11(S)-fluoroepothilone D (750 mg) in 10 mL of 5:1 acetonitrile/water is treated with 48% HF (0.2 mL) for 4 hours at ambient temperature. The mixture is diluted with $CH_2Cl_2$ and washed sequentially with sat. $NaHCO_3$ and brine, then dried over $MgSO_4$, filtered, and evaporated. The product is purified by chromatography on silica gel.

EXAMPLE 19

3,7-bis(O-triethylsilyl)-11(S)-iodoepothilone D

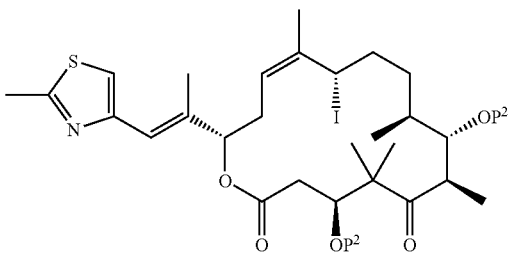

P² = Et₃Si

A solution of the crude 3,7-bis(O-triethylsilyl)-11(R)-(p-toluenesulfonyloxy)epothilone D from Example 16 and lithium iodide (135 mg) in 25 mL of anhydrous methylsulfoxide is heated at 80° C. for 1 hour. The mixture is cooled, dissolved in $CH_2Cl_2$ and washed sequentially with water and brine, then dried over $MgSO_4$, filtered, and evaporated. The product is used without further purification.

EXAMPLE 20

3,7-bis(O-triethylsilyl)-11(R)-fluoroepothilone D

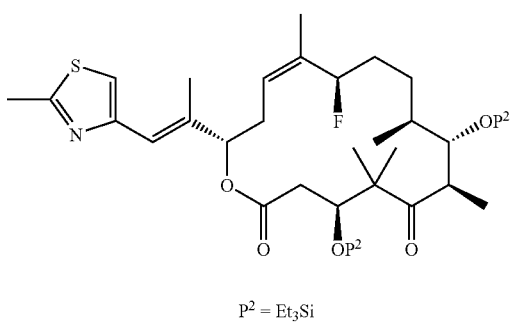

P² = Et₃Si

A solution of the crude protected 11(S)-iodoepothilone from Example 16 and tetrabutylammonium triphenyldifluorosilicate (2.0 g) in 25 mL of anhydrous acetonitrile is heated at 70° C. for 1 hour. The mixture is cooled and evaporated. The residue is dissolved in $CH_2Cl_2$ and washed sequentially with water and brine, then dried over $MgSO_4$, filtered, and evaporated. The product is purified by chromatography on silica gel.

EXAMPLE 21

11(R)-fluoroepothilone D

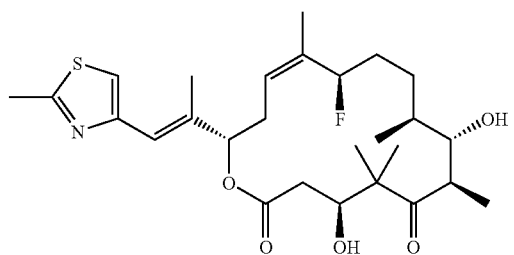

A solution of 3,7-bis(O-triethylsilyl)-11(R)-fluoroepothilone D (750 mg) in 10 mL of 5:1 acetonitrile/water is treated with 48% HF (0.2 mL) for 4 hours at ambient temperature. The mixture is diluted with $CH_2Cl_2$ and washed sequentially with sat. $NaHCO_3$ and brine, then dried over $MgSO_4$, filtered, and evaporated. The product is purified by chromatography on silica gel.

EXAMPLE 22

Liposomal Composition

This example describes liposomal compositions containing 11-fluoro epothilone D. A mixture of lipids and 11-fluoro-epothilone D are dissolved in ethanol and the solution is dried as a thin film by rotation under reduced pressure. The resultant lipid film is hydrated by addition of the aqueous phase and the particle size of the 11-fluoro epothilone D containing liposomes is adjusted to the desired range. Preferably, the mean particle diameter is less than 10 microns, preferably from about 0.5 to about 4 microns. The particle size may be reduced to the desired level, for example, by using mills (e.g., air-jet mill, ball mill, or vibrator mill), microprecipitation, spray-drying, lyophilization, high-pressure homogenization, recrystallization from supercritical media, or by extruding an aqueous suspension of the liposomes through a series of membranes (e.g., polycarbonate membranes) having a selected uniform pore size. In one embodiment, the liposomal composition comprises: an inventive compound (1.00 mg); phosphatidylcholine (16.25 mg); cholesterol (3.75 mg); polyethyleneglycol derivatized distearyl phosphatidylethanolamine (5.00 mg); lactose (80.00 mg); citric acid (4.20 mg); tartaric acid (6.00 mg); NaOH (5.44 mg); water (up to 1 mL). In another embodiment, the liposomal composition comprises: an inventive compound (1.00 mg); phosphatidylcholine (19.80 mg); cholesterol (3.75 mg); distearyl phosphatidylcholine (1.45 mg); lactose (80.00 mg); citric acid (4.20 mg); tartaric acid (6.00 mg); NaOH (5.44 mg); water (up to 1 mL). In yet another embodiment, the liposomal composition comprises: an inventive compound (1.00 mg); 1-palmitoyl-2-oleyl-sn-glycero-3-phosphocholine (17.50 mg); 1-palmitoyl-2-oleyl-sn-glycero-3-phosphoglycerol, Na (7.50 mg); lactose (80.mg); citric acid (4.20 mg); tartaric acid (6.00 mg); NaOH (5.44 mg); water (up to 1 mL). Liposomal compositions containing other compounds of the present invention are prepared using conditions similar to those described above.

EXAMPLE 23

Intravenous Formulation

This example describes an intravenous formuation of 11-fluoro-epothilone D. The formulation contains 10 mg/mL of 11-fluoro-epothilone D in a vehicle containing 30% propylene glycol, 20% Creomophor EL, and 50% ethanol. The vehicle is prepared by measuring ethanol (591.8 g) to a beaker containing a stir bar; adding Creomophor EL (315.0 g) to the solution and mixing for ten minutes; and then adding propylene glycol (466.2 g) to the solution and mixing for another ten minutes. 11-fluoro-epothilone D (1 g) is added to a 1 L volumetric flask containing 400–600 mL of the vehicle and mixed for five minutes. After 11-fluoro epothilone D is in solution, the volume is brought to 1 L; allowed to mix for another ten minutes; and filtered through a 0.22 micron Millipore Millipak filter. The resulting solution is used to aseptically fill sterile 5 mL vials using a metered peristaltic pump to a targeted fill volume of 5.15 mL/vial. The filled vials are immediately stoppered and crimped.

The vial containing 10 mg/mL of 11-fluoro-epothilone D is diluted in normal saline or 5% dextrose solution for administration to patients and administered in non-PVC, non-DEHP bags and administration sets. The product is infused over a one to six hour period to deliver the desired dose.

In one embodiment, the formulation is diluted twenty fold in sterile saline prior to intravenous infusion. The final infusion concentration is 0.5 mg/mL of the inventive compound, 1.5% propylene glycol, 1% Cremophor EL, and 2.5% ethanol which is infused over a one to six hour period to deliver the desired dose.

Intravenous formulations containing other compounds of the present invention may be prepared and used in a similar manner.

EXAMPLE 24

Pretreatment for Cremophor® Toxicity

This example describes a pretreatment regiment for Cremophor® toxicity. Formulations of a compound of the invention that includes Cremophor® may cause toxicity in patients. Pretreatment with steroids can be used to prevent anaphylaxis. Any suitable corticosterioid or combination of corticosteroid with $H_1$ antagonists and/or $H_2$ antagonists may be used. In one embodiment, a subject is premedicated with an oral dose of 50 mg of diphenylhydramine and 300 mg of cimetidine one hour prior to treatment with the inventive compound in a Cremophor® containing formulation. In another embodiment, the subject is premedicated with an intravenous administration of 20 mg of dexamethasone at least one half hour prior to treatment with the inventive compound in a Cremophor® containing formulation. In another embodiment, the subject is premedicated with an intravenous administration of 50 mg of diphenylhydramine, 300 mg of cimetidine and 20 mg of dexamethasone at least one half hour prior to treatment with the inventive compound in a Cremophor® containing formulation. In yet another embodiment, the weight of the subject is taken into account and the subject is pretreated with an administration of diphenylhydramine (5 mg/kg, i.v.); cimetidine (5 mg/kg, i.v).; and dexamethasone (1 mg/kg, i.m.) at least one half hour prior to the treatment with the inventive compound in a Cremophor® containing formulation.

EXAMPLE 25

21,26-dihydroxyepothilone D

HRESITOFMS m/z 524.2699; calcd for $C_{27}H_{42}NO_7S$ $[M+H]^+$, 524.2677. $^1$H NMR (CDCl$_3$, 400 MHz) δ 7.12 (s, 1 H), 6.62 (s, 1 H), 5.46 (dd, J=9.2, 5.6 Hz, 1 H), 5.28 (d, J=6.8 Hz, 1 H), 4.91 (s, 2 H), 4.28 (dd, J=10.8, 2.4 Hz, 1 H), 4.09 (d, J=13.2 Hz, 1 H), 4.01 (d, J=13.2 Hz, 1 H), 3.68 (dd, J=4.0, 2.4 Hz, 1 H), 3.15 (qd, J=6.8, 2.4 Hz, 1 H), 2.68 (overlap, 1 H), 2.65 (dt, J=15.2, 9.2 Hz, 1 H), 2.47 (dd, J=14.8, 11.2 Hz, 1 H), 2.38(m, 1 H), 2.26 (dd, J=14.8, 2.4 Hz, 1 H), 2.23 (overlap. 1 H), 2.12 (m, 2 H), 2.06 (s, 3 H), 1.75 (m, 2 H), 1.38 (m, 1 H) 1.32 (s, 3 H), 1.17 (d, J=6.8 Hz, 3 H), 1.05 (s, 3 H), 1.00 (d, J=7.2 Hz, 3 H).

EXAMPLE 26

14-hydroxyepothilone D

HRESITOFMS mz/z 508.2728; calcd for $C_{27}H_{42}NO_6S$ $[M+H]^+$, 508.2727. $^1$H NMR (CDCl$_3$, 400 MHz) δ 7.02 (s, 1 H), 6.67 (s, 1 H), 5.22 (d, J=9.4 Hz, 1 H), 4.98 (d, J=9.4 Hz, 1 H), 4.57 (t, J=9.2 Hz, 1 H), 4.26 (bro d, J=10.1 Hz, 1 H), 3.70 (m, 1 H), 3.14 (qd, J=6.7, 1.7 Hz, 1 H), 2.70 (s, 3 H), 2.45 (m, 1 H), 2.44 (dd, J=14.3, 11.2 Hz, 1 H), 2.22 (bro d, J=14.3 Hz, 1 H), 2.17 (s, 3 H), 1.96 (m, 1 H), 1.76 (m, 1 H), 1.73 (m, 1 H), 1.72 (s, 3 H), 1.29 (m, 3 H), 1.34 (s, 3 H), 1.20 (d, J=6.8Hz, 3 H), 1.06 (s, 3 H), 1.03 (d, J=7.0, 3 H).

EXAMPLE 27

26-hydroxyepothilone D

HRESITOFMS m/z 508.2723; calcd for $C_{27}H_{42}NO_6S$ $[M+H]^+$, 508.2727. $^1$H NMR (CDCl$_3$, 400 MHz) δ 6.98 (s, 1 H), 6.66 (s, 1 H), 5.45 (dd, J=9.4, 5.8 Hz, 1 H), 5.24 (dd, J=8.8, 2.0 Hz, 1 H), 4.33 (dd, J=11.2, 2.4 Hz, 1 H), 4.09 (d, J=13.2 Hz, 1 H), 4.01 (d, J=13.2 Hz, 1 H), 3.69 (dd, J=4.4, 2.0 Hz, 1 H), 3.18 (qd, J=6.8, 2.4 Hz, 1 H), 2.71 (s, 3 H), 2.63 (dt, J=15.2, 9.2 Hz, 1 H), 2.46 (dd, J=14.8, 11.2 Hz, 1 H), 2.37 (m, 1 H), 2.25 (overlap, 1 H), 2.24 (dd, J=14.8, 2.4 Hz, 1 H), 2.12 (m, 1 H), 2.05 (d, J=1.2 Hz, 3 H), 1.76 (m, 1 H), 1.67 (m, 1 H), 1.36 (s, 3 H), 1.34 (m, 3 H), 1.18 (d, J=6.8Hz, 3 H), 1.05 (s, 3 H), 0.98 (d, J=9.6Hz, 3 H).

EXAMPLE 28

9-hydroxyepothilone D

HRESITOFMS m/z 508.2728; calcd for $C_{27}H_{42}NO_6S$ $[M+H]^+$, 508.2727. $^1$H NMR (CDCl$_3$, 400 MHz) δ 6.96 (s, 1 H), 6.58 (s, 1 H), 5.22 (dd, J=9.1, 2.8 Hz, 1 H), 4.40 (m, 1 H) 4.02 (m, 1 H), 3.76 (d, J=6.2 Hz, 1 H), 3.61 (m, 1 H), 3.30 (qd, J=7.0, 1.8 Hz, 1 H), 2.68 (s, 3 H), 2.62 (m, 1 H), 2.41 (m, 4 H), 2.18 (m, 1 H), 2.06 (d, J=2.1Hz, 3 H), 1.85 (m, 2H), 1.75 (s, 3 H), 1.72 (m, 1 H), 1.35 (s, 3 H), 1.19 (d, J=6.9 Hz, 3 H), 1.05 (s, 3 H), 0.99 (d, J=7.2 Hz, 3 H).

EXAMPLE 29

21-hydroxyepothilone D

HRESITOFMS m/z 508.2713; calcd for $C_{27}H_{42}NO_6S$ $[M+H]^+$, 508.2727. $^1$H NMR (CDCl$_3$, 400 MHz) δ 7.01 (s, 1 H), 6.59 (s, 1 H), 5.34 (m, 1 H), 5.24 (d, J=8.6 Hz, 1 H), 5.13 (dd, J=10.0, 4.9 Hz, 1 H), 4.90 (s, 2 H), 4.30 (dd, J=11.2, 2.7 Hz, 1 H), 3.70 (dd, J=4.0, 2.4 Hz, 1 H), 3.14 (qd, J=6.8, 2.1 Hz, 1 H), 2.62 (dt, J=15.0, 9.8 Hz, 1 H), 2.47 (dd, J=14.7, 11.1 Hz, 1 H), 2.30 (overlap, 1 H), 2.27 (dd, J=14.7, 2.7 Hz, 1 H), 2.06 (s, 3 H), 2.00 (m, 1 H), 1.89 (m, 1 H), 1.75 (m, 1 H), 1.68 (m, 1 H), 1.66 (s, 3 H), 1.33 (s, 3 H), 1.26 (overlap, 3 H), 1.19 (d, J=6.9 Hz, 3 H), 1.05 (s, 3 H), 1.01 (d, J=7.0 Hz, 3 H).

EXAMPLE 30

26-hydroxyepothilone 490

HRESITOFMS m/z 506.2573; calcd for $C_{27}H_{40}NO_6S$ $[M+H]^+$, 506.2571. $^1$H NMR (CDCl$_3$, 400 MHz) δ 6.96 (s, 1 H), 6.59 (s, 1 H), 6.33 (d, J=15.9 Hz, 1 H), 5.95 (td, J=15.9, 7.1 Hz, 1 H), 5.52 (dd, J=9.9, 6.9 Hz, 1 H), 5.29 (dd, J=9.2, 1.9 Hz, 1 H), 4.25 (d, J=12.2 Hz, 1 H), 4.25 (overlap, 1 H), 4.16 (d, J=12.7 Hz, 1 H), 3.70 (dd, J=8.1, 1.8 Hz, 1 H), 3.25 (qd, J=6.9, 1.8 Hz, 1 H), 2.77 (dt, J=14.2, 9.7 Hz, 1 H), 2.69 (s, 3 H), 2.64 (m, 1 H), 2.45 (m, 1 H), 2.43 (dd, J=15.0, 10.7 Hz, 1 H), 2.34 (dd, J=15.0, 2.6 Hz, 1 H), 2.08 (d, J=1.2 Hz, 3 H), 2.07 (overlap, 1 H), 1.96 (m, 1 H), 1.32 (s, 3 H), 1.08 (d, J=6.7 Hz, 3 H), 1.05 (d, J=7.2 Hz, 3 H), 1.04 (s, 3 H).

EXAMPLE 31

21-hydroxyepothilone 490

HRESITOFMS m/z 506.2562; calcd for $C_{27}H_{40}NO_6S$ $[M+H]^+$, 506.2571. $^1$H NMR (CDCl$_3$, 400 MHz) δ 7.12 (s, 1 H), 6.59 (s, 1 H), 6.53 (d, J=15.4 Hz, 1 H), 5.77 (m, 1 H), 5.31 (overlap. 1 H), 5.27 (overlap. 1 H), 4.94 (m, 2 H), 4.20 (dd, J=9.4, 3.7 Hz, 1 H), 3.72 (d, J=6.8 Hz, 1 H), 3.25 (qd, J=7.0, 2.0 Hz, 1 H), 2.87 (overlap. 1 H), 2.82 (dt, J=14.2, 10.5 Hz, 1 H), 2.70 (m. 1 H), 2.56–2.25 (m, 3 H), 2.12 (d, J=1.0 Hz, 3 H), 2.11–1.95 (m, 2 H), 1.80 (s, 3 H), 1.31 (s, 3 H), 1.12 (d, J=6.8 Hz, 3 H), 1.07 (d, J=6.8 Hz, 3 H), 1.04 (s, 3 H).

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

What is claimed is:
1. A bioconversion method comprising the steps of contacting *Amycolata autotrophica* ATCC 35203 with a compound of the structure
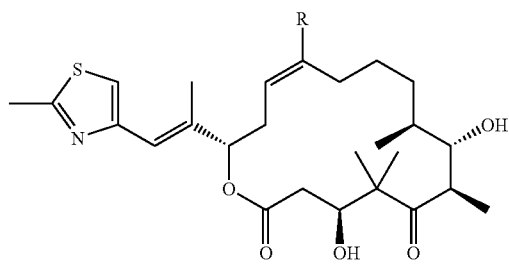
to yield a compound of the structure
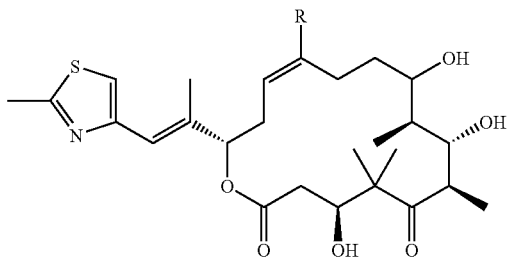
wherein R is hydrogen or methyl.
* * * * *